(12) United States Patent
Ellis et al.

(10) Patent No.: US 7,211,379 B2
(45) Date of Patent: *May 1, 2007

(54) PREVENTION OF MYOCARDITIS, ABORTION AND INTRAUTERINE INFECTION ASSOCIATED WITH PORCINE CIRCOVIRUS-2

(75) Inventors: John Ellis, Saskatoon (CA); Gordon Moore Allan, Belfast (GB); Brian Meehan, Belfast (GB); Edward Clark, Saskatoon (CA); Deborah Haines, Saskatoon (CA); Lori Hassard, Saskatoon (CA); John Harding, Humboldt (CA); Catherine Elisabeth Charreyre, Saint-Laurent de Mure (FR); Gilles Emile Chappuis, Lyons (FR); George Steve Krakowka, Colombus, OH (US); Jean-Christophe Francis Audonnet, Lyons (FR); Francis McNeilly, Newtonards (GB)

(73) Assignee: Merial SAS, Lyons (FR)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 262 days.

This patent is subject to a terminal disclaimer.

(21) Appl. No.: 10/780,318

(22) Filed: Feb. 17, 2004

(65) Prior Publication Data

US 2005/0058653 A1    Mar. 17, 2005

Related U.S. Application Data

(60) Continuation-in-part of application No. 09/680,228, filed on Oct. 6, 2000, now abandoned, which is a continuation-in-part of application No. PCT/EP00/08781, filed on Aug. 28, 2000, and a continuation-in-part of application No. 09/583,350, filed on May 31, 2000, now Pat. No. 6,517,843, application No. 10/780,318, which is a continuation-in-part of application No. 09/884,514, filed on Jun. 19, 2001, now Pat. No. 6,660,272, which is a division of application No. 09/161,092, filed on Sep. 25, 1998, now Pat. No. 6,391,314, which is a continuation-in-part of application No. 09/082,558, filed on May 21, 1998, now Pat. No. 6,368,601.

(60) Provisional application No. 60/151,564, filed on Aug. 31, 1999.

(30) Foreign Application Priority Data

Mar. 10, 1997  (FR) ................... 97 12382
Jan. 22, 1998  (FR) ................... 98 00873
Mar. 20, 1998  (FR) ................... 98 03707

(51) Int. Cl.
C12Q 1/70    (2006.01)
C07H 21/04   (2006.01)
A61K 39/12   (2006.01)

(52) U.S. Cl. .................... 435/5; 435/4; 435/69.1; 424/204.1; 536/23.72

(58) Field of Classification Search .................... None
See application file for complete search history.

(56) References Cited

U.S. PATENT DOCUMENTS

| 6,207,165 | B1 | 3/2001 | Audonnet et al. |
| 6,217,883 | B1 | 4/2001 | Allan et al. |
| 6,368,601 | B1 | 4/2002 | Allan et al. |
| 6,391,314 | B1 | 5/2002 | Allan et al. |
| 6,497,883 | B1 | 12/2002 | Bublot et al. |
| 6,703,023 | B1 | 3/2004 | Jestin et al. |

FOREIGN PATENT DOCUMENTS

| FR | 2772047 | 6/1999 |
| WO | 99/29717 | 6/1999 |
| WO | 99/29871 | 6/1999 |

OTHER PUBLICATIONS

GenBank Accession No. AF027217; Dec. 17, 1997.
GenBank Accession No. AF027217; May 14, 1998.
Nayar et al., Canadian Veterinary Journal, vol. 38, Jun. 1997, pp. 385-386.
E.G. Clark, American Association of Swine Practioners, 1997, pp. 499-501.
Meehan et al., Journal of General Virology, vol. 78, 1997, pp. 221-227.

(Continued)

*Primary Examiner*—Stacy B. Chen
(74) *Attorney, Agent, or Firm*—Anne-Marie C. Yvon; Frommer Lawrence & Haug, LLP

(57) ABSTRACT

Provided is a method for reducing viral load of porcine circovirus type 2 (PCV-2) in a pig by inducing an immune response against PCV-2 through the administration of an immunogenic composition comprising a PCV-2 antigen. A preferred antigen is a vector containing a PCV-2 nucleotide sequence. In a particularly preferred embodiment, the PCV-2 nucleotide sequence is ORF4, ORF13, or ORF4 and ORF13. In some embodiments, the immunogenic composition includes one or more additional pig pathogens.

15 Claims, 8 Drawing Sheets

OTHER PUBLICATIONS

Todd et al., Arch. Virol., vol. 117, 1991, pp. 129-135.
Daft et al., 39th Annual Meeting of American Association of Veterinary Laboratory Diagnosticians, Oct. 12-18, 1996.
Harding et al., American Association of Swine Practioners, 1997, p. 503.
Albina et al., La Semaine Veterinaire des Filieres, No. 26, Nov. 30, 1996, pp. 1-2.
V. Dedet, La Semaine Veterinaire, May 24, 1997, p. 54.
Allan et al., J. Vet. Diagn. Invest., vol. 10 (1998), pp. 3-10.
Ellis et al., Can. Vet. J., vol. 39, Jan. 1998, pp. 44-51.
Segales et al., Veterinary Record, Dec. 6, 1997, pp. 600-601.
Allan et al., Vet. Immunol. Immunopathol., vol. 43 (1994), pp. 357-371.
Allan et al., Vet. Micro., vol. 44 (1995), pp. 49-64.
Tischer et al., Arch. Virol., vol. 91 (1986), pp. 271-276.
Hamel et al., Database EMBL/Genbank/DDBJ, Sep. 26, 1997.
Krakowka et al. 2001. Vet. Pathology 38:31-42.
Allan et al. 2000. J. Vet Diagn. Invest. 12:3-14.
Cruse et al. 1995. Illustrated Dictionary of Immunology. CRC Press, Inc. pp. 156.
Allan et al. 2000. Veterinary Record 147(6): 170-171.
West et al. 1999. J. Vet. Diagn. Invest. 11:530-532.
Bantle, John A. et al. "Phase III Interlaboratory Study of FETAX Part 3. FETAX Validation using 12 Compounds with and without an Exogenous Metabolic Activation System," *Journal of Applied Toxicology*, 19:447-472 (1999).
Fort, Douglas J. et al. "Evaluation of the Developmental Toxicity of Thalidomide Using Frog Embryo Teratogenesis Assay—Xenopus (FETAX): Biotransformation and Detoxification," *Teratogensis, Carcinogenesis, and Mutagenesis*, 20:35-47 (2000).
Newport, John et al. "Major Developmental Transition in Early Xenopus Embryos: I. Characterization and Timing of Cellular Changes at the Midblastula Stage," *Cell*, vol. 30:675-686 (1982).
Newport, John et al. "A Major Developmental Transition in Early Xenopus Embryos: II. Control of the Onset of Transcription," *Cell*, vol. 30:657-696 (1962).
Nakakura, Norihiko et al. "Synthesis of Heterogeneous mRNA-like RNA and Low-Molecular-Weight RNA before the Midblastula Transition in Embryos of *Xenopus laevis*," *Developmental Biology*, 123:421-429 (1987).
Adams, Mark D. et al. "Complementary DNA Sequencing: Expressed Sequence Tags and Human Genome Project," 1651-1656. (1991).
Schena, Mark, et al. "Quantitative Monitoring of Gene Expression Patterns with a Complementary DNA Microarray," *Science*, vol. 270:467-470 (1995).
Schena, Mark et al. "Parallel human genome analysis: Microarray-based expression monitoring of 1000 genes," *Proc. Natl. Acad. Sci. USA*, vol. 93:10614-10619 (1996).
Zhang, Michael Q. "Large-Scale Gene Expression Data Analysis: A New Challenge to Computational Biologists," *Cold Spring Harbor Laboratory*, vol. 9, Issue 8:681-688 (1999).
Nuwaysir, Emile F. et al. "Microarrays and Toxicology: The Advent of Toxicogenomics," *Molecular Carcinogenesis*, 24:153-159 (1999).
Altmann, Curtis R. et al. "Microarray-Based Analysis of Early Development in *Xenopus laevis*," *Developmental Biology*, 236:64-75 (2001).
Nieuwkoop and Faber (1967) External and Internal Stage Criteria in the Development of *Xenopus laevis*, Chapter VII, 162-188.

Figure 1

SEQ ID No. 1

```
aattcaacct taacctttct tattctgtag tattcaaagg gcacagagcg ggggtttgag 60
ccccctcctg ggggaagaaa gtcattaata ttgaatctca tcatgtccac cgcccaggag 120
ggcgttctga ctgtggttcg cttgacagta tatccgaagg tgcgggagag gcgggtgttg 180
aagatgccat ttttccttct ccagcggtaa cggtggcggg ggtggacgag ccaggggcgg 240
cggcggagga tctggccaag atggctgcgg gggcggtgtc ttcttctccg gtaacgcctc 300
cttggatacg tcatatctga aaacgaaaga agtgcgctgt aagtattacc agcgcacttc 360
ggcagcggca gcacctcggc agcacctcag cagcaacatg ccgagcaaga agaatggaag 420
aagcggaccc caacccata aaaggtgggt gttcactctg aataatcctt ccgaagacga 480
gcgcaagaaa atacgggatc ttccaatatc cctatttgat tattttattg ttggcgagga 540
gggtaatgag gaaggacgaa cacctcacct ccaggggttc gctaattttg tgaagaagca 600
gacttttaat aaagtgaagt ggtatttggg tgcccgctgc cacatcgaga aagcgaaagg 660
aacagatcag cagaataaag aatactgcag taaagaaggc aacttactga tggagtgtgg 720
agctcctaga tctcagggac aacggagtga cctgtctact gctgtgagta ccttgttgga 780
gagcgggagt ctggtgaccg ttgcagagca gcaccctgta acgtttgtca gaaatttccg 840
cgggctggct gaactttga aagtgagcgg gaaaatgcag aagcgtgatt ggaagactaa 900
tgtacacgtc attgtgggc cacctgggtg tggtaaaagc aaatgggctg ctaattttgc 960
agacccggaa accacatact ggaaaccacc tagaaacaag tggtgggatg gttaccatgg 1020
tgaagaagtg gttgttattg atgacttta tggctggctg ccctgggatg atctactgag 1080
actgtgtgat cgatatccat tgactgtaga gactaaaggt ggaactgtac cttttttggc 1140
ccgcagtatt ctgattacca gcaatcagac cccgttggaa tggtactcct caactgctgt 1200
cccagctgta gaagctcttt atcggaggat tacttccttg gtattttgga agaatgctac 1260
agaacaatcc acggaggaag ggggccagtt cgtcacccct tccccccat gccctgaatt 1320
tccatatgaa ataaattact gagtctttt tatcacttcg taatggtttt tattattcat 1380
taagggttaa gtgggggtc tttaagatta aattctctga attgtacata catggttaca 1440
cggatattgt attcctggtc gtatatactg ttttcgaacg cagtgccgag gcctacgtgg 1500
tctacatttc cagcagtttg tagtctcagc cacagctggt ttcttttgtt gtttggttgg 1560
aagtaatcaa tagtggaatc taggacaggt ttggggggtaa agtagcggga gtggtaggag 1620
aagggctggg ttatggtatg gcgggaggag tagtttacat aggggtcata ggtgagggct 1680
gtggcctttg ttacaaagtt atcatctaga ataacagcac tggagcccac tcccctgtca 1740
ccctgggtga tcggggagca gggccag                                    1767
```

Figure 2

SEQ ID No. 2

```
aattcaacct taacctttct tattctgtag tattcaaagg gcacagagcg ggggtttgag   60
cccctcctg ggggaagaaa gtcattaata ttgaatctca tcatgtccac cgcccaggag  120
ggcgttttga ctgtggttcg cttgacagta tatccgaagg tgcgggagag gcgggtgttg  180
aagatgccat ttttccttct ccagcggtaa cggtggcggg ggtggacgag ccaggggcgg  240
cggcggagga tctggccaag atggctgcgg gggcggtgtc ttcttctccg gtaacgcctc  300
cttggatacg tcatatctga aaacgaaaga agtgcgctgt aagtattacc agcgcacttc  360
ggcagcggca gcacctcggc agcacctcag cagcaacatg cccagcaaga agaatggaag  420
aagcggaccc caaccccata aaaggtgggt gttcactctg aataatcctt ccgaagacga  480
gcgcaagaaa atacgggatc ttccaatatc cctatttgat tattttattg ttggcgagga  540
gggtaatgag gaaggacgaa cacctcacct ccaggggttc gctaattttg tgaagaagca  600
gactttaat aaagtgaagt ggtatttggg tgcccgctgc cacatcgaga aagcgaaagg  660
aacagatcag cagaataaag aatactgcag taagaaggc aacttactga tggagtgtgg  720
agctcctaga tctcagggac aacggagtga cctgtctact gctgtgagta ccttgttgga  780
gagcgggagt ctggtgaccg ttgcagagca gcaccctgta acgtttgtca gaaatttccg  840
cgggctggct gaacttttga aagtgagcgg gaaaatgcag aagcgtgatt ggaagactaa  900
tgtacacgtc attgtggggc cacctgggtg tggtaaaagc aaatgggctg ctaattttgc  960
agacccggaa accacatact ggaaaccacc tagaaacaag tggtgggatg gttaccatgg 1020
tgaagaagtg gttgttattg atgactttta tggctggctg ccctgggatg atctactgag 1080
actgtgtgat cgatatccat tgactgtaga gactaaaggt ggaactgtac cttttttggc 1140
ccgcagtatt ctgattacca gcaatcagac cccgttggaa tggtactcct caactgctgt 1200
cccagctgta gaagctcttt atcggaggat tacttccttg gtattttgga agaatgctac 1260
agaacaatcc acggaggaag ggggccagtt cgtcacccat tcccccccat gccctgaatt 1320
tccatatgaa ataaattact gagtcttttt tatcacttcg taatggtttt tattattcat 1380
taagggttaa gtgggggggtc tttaagatta aattctctga attgtacata catggttaca 1440
cggatattgt attcctggtc gtatatactg ttttcgaacg cagtgccgag gcctacgtgg 1500
tctacatttc cagtagtttg tagtctcagc cacagctgat ttctttgtt gtttggttgg 1560
aagtaatcaa tagtggaatc taggacaggt ttgggggtaa agtagcggga gtggtaggag 1620
aagggctggg ttatggtatg gcgggaggag tagtttacat aggggtcata ggtgagggct 1680
gtggcctttg ttacaaagtt atcatctaga ataacagcac tggagcccac tcccctgtca 1740
ccctgggtga tcggggagca gggccag                                    1767
```

Figure 3

SEQ ID No. 3

```
aattcaacct taaccttttt tattctgtag tattcaaagg gtatagagat tttgttggtc   60
cccctcccg ggggaacaaa gtcgtcaata ttaaatctca tcatgtccac cgcccaggag  120
ggcgttctga ctgtggtagc cttgacagta tatccgaagg tgcgggagag gcgggtgttg  180
aagatgccat ttttccttct ccaacggtag cggtggcggg ggtggacgag ccaggggcgg  240
cggcggagga tctggccaag atggctgcgg gggcggtgtc ttcttctgcg gtaacgcctc  300
cttggatacg tcatagctga aaacgaaaga agtgcgctgt aagtattacc agcgcacttc  360
ggcagcggca gcacctcggc agcacctcag cagcaacatg cccagcaaga agaatggaag  420
aagcggaccc caaccacata aaaggtgggt gttcacgctg aataatcctt ccgaagacga  480
gcgcaagaaa atacgggagc tcccaatctc cctatttgat tattttattg ttggcgagga  540
gggtaatgag gaaggacgaa caccctcacct ccaggggttc gctaattttg tgaagaagca  600
aactttaat aaagtgaagt ggtatttggg tgcccgctgc cacatcgaga aagccaaagg  660
aactgatcag cagaataaag aatattgcag taaagaaggc aacttactta ttgaatgtgg  720
agctcctcga tctcaaggac aacggagtga cctgtctact gctgtgagta ccttgttgga  780
gagcgggagt ctggtgaccg ttgcagagca gcaccctgta acgtttgtca gaaatttccg  840
cgggctggct gaacttttga aagtgagcgg gaaaatgcag aagcgtgatt ggaagaccaa  900
tgtacacgtc attgtggggc cacctgggtg tggtaaaagc aaatgggctg ctaattttgc  960
agacccggaa accacatact ggaaaccacc tagaaacaag tggtgggatg gttaccatgg 1020
tgaagaagtg gttgttattg atgacttta tggctggctg ccgtgggatg atctactgag 1080
actgtgtgat cgatatccat tgactgtaga gactaaaggt ggaactgtac cttttttggc 1140
ccgcagtatt ctgattacca gcaatcagac cccgttggaa tggtactcct caactgctgt 1200
cccagctgta gaagctctct atcggaggat tacttccttg gtattttgga agaatgctac 1260
agaacaatcc acggaggaag ggggccagtt cgtcacccct tcccccccat gccctgaatt 1320
tccatatgaa ataaattact gagtctttt tatcacttcg taatggtttt tattattcat 1380
ttagggttta agtgggggt ctttaagatt aaattctctg aattgtacat acatggttac 1440
acggatattg tagtcctggt cgtatatact gttttcgaac gcagtgccga ggcctacgtg 1500
gtccacattt ctagaggttt gtagcctcag ccaaagctga ttccttttgt tatttggttg 1560
gaagtaatca atagtggagt caagaacagg tttgggtgtg aagtaacggg agtggtagga 1620
gaagggttgg gggattgtat ggcgggagga gtagtttaca tatgggtcat aggttagggc 1680
tgtggccttt gttacaaagt tatcatctag aataacagca gtggagccca ctcccctatc 1740
accctgggtg atggggagc agggccag                                    1768
```

Figure 4

SEQ ID No. 4

```
aattcaacct taaccttct tattctgtag tattcaaagg gtatagagat tttgttggtc  60
cccctcccg ggggaacaaa gtcgtcaatt ttaaatctca tcatgtccac cgcccaggag 120
ggcgttgtga ctgtggtacg cttgacagta tatccgaagg tgcgggagag gcgggtgttg 180
aagatgccat ttttccttct ccaacggtag cggtggcggg ggtggacgag ccaggggcgg 240
cggcggagga tctggccaag atggctgcgg gggcggtgtc ttcttctgcg gtaacgcctc 300
cttggatacg tcatagctga aaacgaaaga agtgcgctgt aagtattacc agcgcacttc 360
ggcagcggca gcacctcggc agcacctcag cagcaacatg cccagcaaga agaatggaag 420
aagcggaccc caaccacata aaggtgggt gttcacgctg aataatcctt ccgaagacga 480
gcgcaagaaa atacgggagc tcccaatctc cctatttgat tattttattg ttggcgagga 540
gggtaatgag gaaggacgaa cacctcacct ccaggggttc gctaattttg tgaagaagca 600
aactttaat aaagtgaagt ggtatttggg tgcccgctgc cacatcgaga aagccaaagg 660
aactgatcag cagaataaag aatattgcag taaagaaggc aacttactta ttgaatgtgg 720
agctcctcga tctcaaggac aacggagtga cctgtctact gctgtgagta ccttgttgga 780
gagcgggagt ctggtgaccg ttgcagagca gcaccctgta acgtttgtca gaaatttccg 840
cgggctggct gaactttga aagtgagcgg gaaaatgcag aagcgtgatt ggaagaccaa 900
tgtacacgtc attgtggggc caccctgggtg tggtaaaagc aaatgggctg ctaattttgc 960
agacccggaa accacatact ggaaaccacc tagaacaag tggtgggatg gttaccatgg 1020
tgaagaagtg gttgttattg atgactttta tggctggctg ccgtgggatg atctactgag 1080
actgtgtgat cgatatccat tgactgtaga gactaaaggt ggaactgtac cttttttggc 1140
ccgcagtatt ctgattacca gcaatcagac cccgttggaa tggtactcct caactgctgt 1200
cccagctgta gaagctctct atcggaggat tacttccttg gtattttgga agaatgctac 1260
agaacaatcc acggaggaag ggggccagtt cgtcaccctt tccccccat gccctgaatt 1320
tccatatgaa ataaattact gagtcttttt tatcacttcg taatggtttt tattattcat 1380
ttagggttta agtgggggt ctttaagatt aaattctctg aattgtacat acatggttac 1440
acggatattg tagtcctggt cgtatttact gttttcgaac gcagcgccga ggcctacgtg 1500
gtccacattt ccagaggttt gtagtctcag ccaaagctga ttccttttgt tatttggttg 1560
gaagtaatca atagtggagt caagaacagg tttgggtgtg aagtaacggg agtggtagga 1620
gaagggttgg gggattgtat ggcgggagga gtagtttaca tatgggtcat aggttagggc 1680
tgtggccttt gttacaaagt tatcatctag aataacagca gtggagccca ctccctatc 1740
accctgggtg atggggagc agggccag                                    1768
```

Figure 5

SEQ ID No. 5

```
aattcatatt tagcctttct aatacggtag tattggaaag gtaggggtag ggggttggtg    60
ccgcctgagg gggggaggaa ctggccgatg ttgaatttga ggtagttaac attccaagat   120
ggctgcgagt atcctccttt tatggtgagt acaaattctg tagaaaggcg ggaattgaag   180
atacccgtct ttcggcgcca tctgtaacgg tttctgaagg cggggtgtgc caaatatggt   240
cttctccgga ggatgtttcc aagatggctg cgggggcggg tccttcttct gcggtaacgc   300
ctccttggcc acgtcatcct ataaaagtga aagaagtgcg ctgctgtagt attaccagcg   360
cacttcggca gcggcagcac ctcggcagcg tcagtgaaaa tgccaagcaa gaaaagcggc   420
ccgcaaccccc ataagaggtg ggtgttcacc cttaataatc cttccgagga ggagaaaaac   480
aaaatacggg agcttccaat ctccctttt gattattttg tttgcggaga ggaaggtttg   540
gaagagggta gaactcctca cctccagggg tttgcgaatt ttgctaagaa gcagactttt   600
aacaaggtga agtggtattt tggtgcccgc tgccacatcg agaaagcgaa aggaaccgac   660
cagcagaata agaatactg cagtaaagaa ggccacatac ttatcgagtg tggagctccg   720
cggaaccagg ggaagcgcag cgacctgtct actgctgtga gtacccttt ggagacgggg   780
tctttggtga ctgtagccga gcagttccct gtaacgtatg tgagaaattt ccgcgggctg   840
gctgaacttt tgaaagtgag cgggaagatg cagcagcgtg attggaagac agctgtacac   900
gtcatagtgg gcccgcccgg ttgtgggaag agccagtggg cccgtaattt tgctgagcct   960
agggacacct actggaagcc tagtagaaat aagtggtggg atggatatca tggagaagaa  1020
gttgttgttt tggatgattt ttatggctgg ttaccttggg atgatctact gagactgtgt  1080
gaccggtatc cattgactgt agagactaaa gggggtactg ttcctttttt ggcccgcagt  1140
attttgatta ccagcaatca ggcccccccag gaatggtact cctcaactgc tgtcccagct  1200
gtagaagctc tctatcggag gattactact ttgcaatttt ggaagactgc tggagaacaa  1260
tccacggagg tacccgaagg ccgatttgaa gcagtggacc caccctgtgc ccttttccca  1320
tataaaataa attactgagt cttttttgtt atcacatcgt aatggttttt attttattt  1380
atttagaggg tcttttagga taaattctct gaattgtaca taaatagtca gccttaccac  1440
ataatttgg gctgtggctg catttggag cgcatagccg aggcctgtgt gctcgacatt  1500
ggtgtgggta tttaaatgga gccacagctg gtttctttta ttatttgggt ggaaccaatc  1560
aattgtttgg tccagctcag gtttggggt gaagtacctg gagtggtagg taaagggct  1620
ccttatggtg tggcgggagg agtagttaat atagggtca taggccaagt tggtggaggg  1680
ggttacaaag ttggcatcca agataacaac agtggaccca acacctcttt gattagaggt  1740
gatggggtct ctggggtaa                                                1759
```

Figure 6

SEQ ID No. 6

```
gaattcaacc ttaaccttttt ttattctgta gtattcaaag ggtataaaga ttttgttggt 60
ccccctccc gggggaacaa agtcgtcaat attaaatctc atcatgtcca ccgcccagga 120
gggcgttctg actgtggtag ccttgacagt atatccgaag gtgcgggaga rgcgggtgtt 180
gaaaatgcca tttttccttc tccaacggta gcggtggcgg gggtggacma nccacgggcg 240
gcggcggawg atctggccaa gatggctgcg ggggcggtgt cttcttctgc ggtaacgcct 300
ccttggatac gtcatagctg aaaacgaaag aagtgcgctg taagtattac cagcgcactt 360
cggcagcggc agcacctcgg cagcacctca gcagcaacat gcccagcaag aagaatggaa 420
gaagcggacc ccaaccacat aaaaggtggg tgttcacgct gaataatcct tccgaagacg 480
agcgcaagaa aatacgggag ctcccaatct ccctatttga ttatttttatt gttggcgagg 540
agggtwwtga ggaangacga acacctcacc tccaggggtt cgctaatttt gtgaagaagc 600
aaacttttaa taaagtgaag tggtatttgg gtgcccgctg ccacatcgag aaagccaaag 660
gaactgatca gcagaataaa gaatattgca gtaaagaagg caacttactt attgaatgtg 720
gagctcctcg atctcaagga caacgagtg acctgtctac tgctgtgagt accttgttgg 780
agagcgggag tctggtgacc gttgcagagc agcaccctgt aacgtttgtc agaaatttcc 840
gcgggctggc tgaactttttg aaagtgagcg ggaaaatgca gaagcgtgat tggaagacca 900
atgtacacgt cattgtgggg ccacctgggt gtggtaaaag caaatgggct gctaattttg 960
cagacccgga aaccacatac tggaaaccac ctagaaacaa gtggtgggat ggttaccatg 1020
gtgaagaagt ggttgttatt gatgactttt atggctggct gccgtgggat gatctactga 1080
gactgtgtga tcgatatcca ttgactgtag agactaaagg tggaactgta cnnnnnnngg 1140
cccgcagtat tctgattacc agcaatcaga ccccgttgga atggtactcc tcaactgctg 1200
tcccagctgt agaagctctc tatcggagga ttacttcctt ggtattttgg aagaatgcta 1260
cagaacaatc cacggaggaa gggggccagt tngtcaccct ttcccccccca tgccctgaat 1320
ttccatatga aataaattac tgagtctttt ttatcacttc gtaatggttt ttattattca 1380
tttagggttt aagtgggggg tcttttaagat taaattctct gaattgtaca tacatggtta 1440
cacggatatt gtagtcctgg tcgtatatac tgttttcgaa cgcagtgccg aggcctacgt 1500
ggtccacatt tctagaggtt tgtagcctca gccaaagctg attccttttg ttatttggtt 1560
ggaagtaatc aatagtggag tcaagaacag gtttgggtgt gaagtaacgg gagtggtagg 1620
agaagggttg ggggattgta tggcgggagg agtagtttac atatgggtca taggttaggg 1680
ctgtggcctt tgttacaaag ttatcatcta gaataacagc agtggagccc actcccctat 1740
caccctgggt gatggggag cagggcca                                    1768
```

Figure 7

SEQ ID No. 7

```
accagcgcac ttcggcagcg gcagcacctc ggcagcacct cagcagcaac atgcccagca 60
agaagaatgg aagaagcgga ccccaaccac ataaaaggtg ggtgttcacg ctgaataatc 120
cttccgaaga cgagcgcaag aaaatacggg agctcccaat ctccctattt gattatttta 180
ttgttggcga ggagggtaat gaggaaggac gaacacctca cctccagggg ttcgctaatt 240
ttgtgaagaa kcaaactttt aataaagtga agtggtattt gggtgcccgc tgccacatcg 300
agaaagccaa aggaactgat cagcagaata aagaatattg cagtaaagaa ggcaacttac 360
ttattgaatg tggagctcct cgatctcaag gacaacggag tgacctgtct actgctgtga 420
gtaccttgtt ggagagcggg agtctggtga ccgttgcaga gcagcaccct gtaacgtttg 480
tcagaaattt ccgcgggctg gctgaacttt tgaaagtgag cgggaaaatg cagaagcgtg 540
attggaagac caatgtacac gtcattgtgg ggccacctgg gtgtggtaaa agcaaatggg 600
ctgctaattt tgcagacccg gaaaccacat actggaaacc acctagaaac aagtggtggg 660
atggttacca tggtgaagaa gtggttgtta ttgatgactt ttatggctgg ctgccgtggg 720
atgatctact gagactgtgt gatcgatatc cattgactgt agagactaaa ggtggaactg 780
tacctttttt ggcccgcagt attctgatta ccagcaatca gaccccgttg gaatggtact 840
cctcaactgc tgtcccagct gtagaagctc tctatcggag gattacttcc ttggtatttt 900
ggaagaatgc tacagaacaa tccacggagg aaggggccca gttcgtcacc ctttcccccc 960
catgccctga atttccatat gaaataaatt actgagtcyt ttttatcact tcgtaatggt 1020
ttttattatt catttagggg ttaagtgggg ggtctttaag attaaattcc ctgaattgta 1080
catacagggt tacacggata ttgtagtcct ggtcgtattt actgttttcg aacgcagtgc 1140
cgaggcctac gtggtccaca tttctagagg tttgtagcct cagccaaagc tgattccttt 1200
tgttatttgg ttggaagtaa tcaatagtgg agtcaagaac aggtttgggt gtgaagtaac 1260
gggagtggta ggagaagggt tggggattg tatggcggga ggagtagttt acatatgggt 1320
catatgtttg ggctgtggcc tttggtacaa agttatcatc tagaataaca gcagtggagc 1380
ccactcccct atcaccctgg gtgatggggg agcagggcca gaattcaacc ttaacctttc 1440
ttattctgta gtattcaaag ggtatagaga ttttgttggt ccccccctcc gggggaacaa 1500
agtcgtcaat tttaaatctc atcatgtcca ccgcccagga gggcgttgtg actgtggtac 1560
gcttgacagt atatccgaag gtgcgggaga ggcgggtgtt gaagatgcca ttttttccttc 1620
tccaacggta gcggtggcgg gggtggacga gccaggggcg gcggcggagg atctggccaa 1680
gatggctgcg ggggcggtgt cttcttctgc ggtaacgcct ccttggatat gtcatagctg 1740
aaaacgaaag aagtgcgctg taagtatt                                    1768
```

Figure 8

SEQ ID No. 8

```
accagcgcac ttcggcagcg gcagcacctc ggcagcacct cagcagcaac atgcccagca 60
agaagaatgg aagaagcgga ccccaaccac ataaaaggtg ggtgttcacg ctgaataatc 120
cttccgaaga cgagcgcaag aaaatacggg agctcccaat ctccctattt gattatttta 180
ttgttggcga ggagggtaat gaggaaggac gaacacctca cctccagggg ttcgctaatt 240
ttgtgaagaa gcaaactttt aataaagtga agtggtattt gggtgcccgc tgccacatcg 300
agaaagccaa aggaactgat cagcagaata aagaatattg cagtaaagaa ggcaacttac 360
ttattgaatg tggagctcct cgatctcaag gacaacggag tgacctgtct actgctgtga 420
gtaccttgtt ggagagcggg agtctggtga ccgttgcaga gcagcaccct gtaacgtttg 480
tcagaaattt ccgcgggctg gctgaacttt tgaaagtgag cgggaaaatg cagaagcgtg 540
attggaagac caatgtacac gtcattgtgg ggccacctgg gtgtggtaaa agcaaatggg 600
ctgctaattt tgcagacccg gaaaccacat actggaaacc acctagaaac aagtggtggg 660
atggttacca tggtgaagaa gtggttgtta ttgatgactt tatggctgg ctgccgtggg 720
atgatctact gagactgtgt gatcgatatc cattgactgt agagactaaa ggtggaactg 780
taccttttt ggcccgcagt attctgatta ccagcaatca gaccccgttg gaatggtact 840
cctcaactgc tgtcccagct gtagaagctc tctatcggag gattacttcc ttggtatttt 900
ggaagaatgc tacagaacaa tccacggagg aaggggggcca gttcgtcacc ctttccccccc 960
catgccctga atttccatat gaaataaatt actgagtctt ttttatcact tcgtaatggt 1020
ttttattatt catttagggg ttaagtgggg ggtctttaag attaaattct ctgaattgta 1080
catacatggt tacacggata ttgtagtcct ggtcgtattt actgttttcg aacgcagtgc 1140
cgaggcctac gtggtccaca tttctagagg tttgtagcct cagccaaagc tgattccttt 1200
tgttatttgg ttggaagtaa tcaatagtgg agtcaagaac aggtttgggt gtgaagtaac 1260
gggagtggta ggagaagggt tggggggattg tatggcggga ggagtagttt acatatgggt 1320
cataggttag ggctgtggcc tttggtacaa agttatcatc tagaataaca gcagtggagc 1380
ccactcccct atcaccctgg gtgatggggg agcagggcca gaattcaacc ttaaccttt 1440
ttattctgta gtattcaaag ggtatagaga ttttgttggt ccccccctccc gggggaacaa 1500
agtcgtcaat tttaaatctc atcatgtcca ccgcccagga gggcgttgtg actgtagtac 1560
gcttgacagt atatccgaag gtgcgggaga ggcgggtgtt gaagatgcca ttttccttc 1620
tccaacggta gcggtggcgg gggtggacga gccagggcg gcggcggagg atctggccaa 1680
gatggctgcg ggggcggtgt cttcttctgc ggtaacgcct ccttggatac gtcatagctg 1740
aaaacgaaag aagtgcgctg taagtatt                                    1768
```

PREVENTION OF MYOCARDITIS, ABORTION AND INTRAUTERINE INFECTION ASSOCIATED WITH PORCINE CIRCOVIRUS-2

RELATED APPLICATIONS

This application is a continuation-in-part of U.S. application Ser. No. 09/680,228, filed Oct. 6, 2000 now abandoned, which is a continuation-in-part of International application No. PCT/EP00/08781, filed Aug. 28, 2000, and published as WO 01/16330 on Mar. 8, 2001, and of U.S. application Ser. No. 09/583,350, filed May 31, 2000, now U.S. Pat. No. 6,517,843, which claims priority to and is based upon U.S. application Ser. No. 60/151,564, filed Aug. 31, 1999. This application is also a continuation-in-part of U.S. application Ser. No. 09/884,514, filed Jun. 19, 2001, now U.S. Pat. No. 6,660,272, which is a divisional of U.S. application Ser. No. 09/161,092, filed Sep. 25, 1998, now U.S. Pat. No. 6,391,314, which is a continuation-in-part of U.S. application Ser. No. 09/082,558, filed May 21, 1998, now U.S. Pat. No. 6,368,601, which claims priority from French application Nos. 98/03707, filed Mar. 20, 1998; 98/00873, filed Jan. 22, 1998; and 97/12382, filed Oct. 3, 1997.

Reference is also made to Internation application No. PCT/EP99/04698, filed Jun. 28, 1999, published as WO 00/01409 on Jan. 13, 2000, and to U.S. application Ser. No. 09/784,962, filed Feb. 16, 2001, which is a divisional of U.S. application Ser. No. 09/347,594, filed Jul. 1, 1999, now U.S. Pat. No. 6,217,883, all of which claim priority to French application No. 98/08777, filed Jul. 6, 1998. Reference is further made to International application No. PCT/FR98/02107, filed Oct. 1, 1998, and published as WO 99/18214 on Apr. 15, 1994, and to U.S. application Ser. No. 09/586,535, filed May 31, 2000, claiming priority to U.S. application Ser. No. 60/138,352 filed Jun. 10, 1999, and to U.S. application Ser. No. 09/583,545, filed Jun. 1, 2000, now U.S. Pat. No. 6,497,883, claiming priority to U.S. application Ser. No. 60/138,478, filed Jun. 10, 1999. Reference is made to U.S. application Ser. No. 09/232,468, filed Jan. 15, 1999, which is a continuation-in-part of International application No. PCT/FR97/01313, filed Jul. 15, 1997, published as WO 98/03658 on Jan. 29, 1998, claiming priority to French application No. 96/09338, filed Jul. 19, 1996. Mention is also made of International application PCT/CA98/01130, filed Dec. 11, 1998 and published as WO99/29717 on Jun. 17, 1999, and of U.S. application Ser. No. 10/653,849, filed Sep. 2, 2003.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The invention relates to methods and/or compositions for the prevention and/or treatment of PCV-2-caused myocarditis, and/or abortion and/or intrauterine infection, as well as pathologic sequelae including but not limited to post-weaning multisystemic wasting syndrome; and, to methods for preparing such compositions and kits for preparing such compositions or for performing such methods, inter alia.

Various documents are cited in this text. Citations in the text can be by way of a citation to a document in the reference list, e.g., by way of an author(s) and document year citation to a document listed in the reference list, or by full citation in the text to a document that may or may not also be listed in the reference list.

There is no admission that any of the various documents cited in this text are prior art as to the present invention. Any document having as an author or inventor person or persons named as an inventor herein is a document that is not by another as to the inventive entity herein. All documents cited in this text ("herein cited documents") and all documents cited or referenced in herein cited documents are hereby incorporated herein by reference.

BACKGROUND OF THE INVENTION

Porcine circovirus-2 (PCV-2) was recently identified as an agent that has been consistently associated with post-weaning multisystemic wasting syndrome (PMWS) in swine populations in several parts of the world (Allan et al. 1998; Ellis et al., 1998). Isolates of PCV-2 obtained from infected pigs in several countries are virtually identical genetically, and are distinctly different from the PCV (CCL33, PCV-1) that was originally identified in the 1970's as a noncytopathic contaminant of porcine kidney (PK/15) cell line (Meehan et al. 1998; Tischer et al. 1974). Pigs with naturally acquired or experimentally induced PCV-2 infections present with progressive weight loss, tachypnea, dyspnea, and jaundice (Allan et al. 1998; Allan et al. 1999; Ellis et al. 1998; Ellis et al. 1999). Gross pathologic findings that have been directly associated with PCV-2 antigen include, lymphadenopathy, interstitial pneumonia, hepatitis and nephritis (Allan et al. 1998; Allan et al. 1999; Ellis et al. 1998; Ellis et al. 1999). PCV-2 has not heretofore been directly linked to abortion or lesions in fetal pigs. Thus, heretofore, it has not been proposed to address the issue of PCV-2-caused myocarditis, and/or abortion and/or intrauterine infection.

OBJECTS AND SUMMARY OF THE INVENTION

It has surprisingly been found that PCV-2 is a causative agent of myocarditis, abortion and intrauterine infection, as well as post-weaning multisystemic wasting syndrome.

By definition, a PCV-2 immunogen is intended to encompass live attenuated or inactivated PCV-2, or subunit(s) from PCV-2 obtained by in vitro expression or by extraction, or fragment(s) comprising at least one epitope of interest which can be obtained by chemical synthesis or by in vitro recombinant expression, as well as recombinant vector(s) comprising and expressing in vivo sequence(s) or fragment(s) or epitope(s) of PCV-2 genome as herein disclosed or as in documents cited or referenced herein.

A similar definition applies for an immunogen of another porcine pathogen as disclosed herein.

Thus, an object of the invention can be to provide methods and/or compositions for the prevention and/or treatment of PCV-2-caused myocarditis, and/or abortion and/or intrauterine infection, as well as post-weaning multisystemic wasting syndrome and/or pathologic sequelae including but not limited to post-weaning multisystemic wasting syndrome; and, methods for formulating such compositions and uses of a PCV-2 immunogen (which compositions can also include a porcine parvovirus (PPV) immunogen, wherein when recombinant vector expression is used, the vector can co-express both the PPV and the PCV-2 immunogens, inter alia) for formulating such compositions.

Another object of the invention is the isolation and characterisation of new PCV-2 strains identified 1103 (1103/1 P.2) and 1121 (1121/1 P.1), and their uses to produce immunogens, as well as antigens and antibodies for diagnostics, in relation with PCV-2-caused myocarditis, and/or abortion and/or intrauterine infection, as well as post-weaning multisystemic wasting syndrome and/or pathologic sequelae associated therewith.

The invention provides also for inoculation of female pigs (e.g., sows, gilts) with a composition comprising a (at least one) PCV-2 immunogen (which composition can also include an immunogen from porcine parvovirus) prior to breeding; and/or prior to serving, and/or during gestation (or pregnancy); and/or prior to the perinatal period or farrowing; and/or repeatedly over a lifetime, to prevent myocarditis and/or abortion and/or intrauterine infection associated with PCV-2, as well as post-weaning multisystemic wasting syndrome and other pathologic sequelae associated with PCV-2; or, to elicit an immunogenic or protective response against PCV-2 and thereby prevent post-weaning multisystemic wasting syndrome and/or myocarditis and/or abortion and/or intrauterine infection associated with porcine circovirus-2 and/or other pathologic sequelae associated with PCV-2.

Advantageously, at least one inoculation is done before serving. It is also advantageously followed by an inoculation to be performed during gestation, e.g., at about mid-gestation (at about 6–8 weeks of gestation) and/or at the end of gestation (at about 11–13 weeks of gestation). Thus, an advantageous regimen is an inoculation before serving and a booster inoculation during gestation. Thereafter, there can be reinoculation before each serving and/or during gestation at about mid-gestation (at about 6–8 weeks of gestation) and/or at the end of gestation (at about 11–13 weeks of gestation). Preferably, reinoculation can be during gestation only.

In another preferred embodiment, piglets, such as piglets from vaccinated females (e.g., inoculated as herein discussed), are inoculated within the first weeks of life, e.g., inoculation at one and/or two and/or three and/or four and/or five weeks of life. More preferably, piglets are first inoculated within the first week of life or within the third week of life (e.g., at the time of weaning). Even more advantageous, such piglets are then boosted two (2) to four (4) weeks later (after being first inoculated). Thus, both offspring, as well as female pig (e.g., sow, gilt) can be administered compositions of the invention and/or can be the subject of performance of methods of the invention.

Thus, the invention also comprehends immunogenic or vaccine compositions for preventing or treating myocarditis and/or abortion and/or intrauterine infection associated with porcine circovirus-2, as well as post-weaning multisystemic wasting syndrome and other pathologic sequelae associated with PCV-2. An immunogenic (or immunological) composition elicits an immunological response—local or systemic. A vaccine composition elicits a local or systemic protective response. The terms "immunological composition" and "immunogenic composition" include a "vaccine composition" (as the two former terms can be protective compositions). The composition can comprise a PCV-2 immunogen (which composition can also include a PPV immunogen).

And, the invention further comprehends uses of a PCV-2 immunogen (which composition can also include a PPV immunogen) to formulate an immunogenic or vaccine composition for preventing or treating myocarditis and/or abortion and/or intrauterine infection associated with porcine circovirus-2, as well as post-weaning multisystemic wasting syndrome and other pathologic sequelae associated with PCV-2.

Further still, the invention comprehends an immunogenic or vaccine composition for the prevention and/or treatment of PCV-2-caused myocarditis, and/or abortion and/or intrauterine infection and/or post-weaning multisystemic wasting syndrome comprising a pharmaceutically or veterinarily acceptable carrier and/or vehicle and/or excipient and/or adjuvant, and a PCV-2 immunogen The composition can additionally include at least one immunogen from at least one additional pig pathogen, e.g.: Porcine Reproductive and Respiratory Syndrome (PRRS), *Mycoplasma hyopneumoniae, Actinobacillus pleuropneumoniae, E. coli, Bordetella bronchiseptica, Pasteurella multocida, Erysipelothrix rhusiopathiae*, Pseudorabies, Hog cholera, Swine Influenza, and Porcine Parvovirus (PPV). Thus, vector-based compositions can include at least one immunogen from at least one additional pig pathogen, such as a vector expressing a sequence from this pathogen, wherein the vector can also be the vector expressing the PCV-2 immunogen. The vector expressing a PCV-2 sequence can comprise a PCV-2 sequence or fragment thereof as herein disclosed or as in documents cited or referenced herein; and the invention comprehends such nucleic acid molecules, vectors containing them, compositions comprising such nucleic acid molecules or vector expression products from such nucleic acid molecules, compositions comprising such expression products, probes or primers for such nucleic acid molecules, and methods for making and using any or all of the foregoing.

The vector can comprise a DNA vector plasmid, a bacteria such as an *E. coli*, a virus such as baculovirus, a herpesvirus including pig herpes viruses, including Aujeszky's disease virus, an adenovirus including a porcine adenovirus, a poxvirus, including a vaccinia virus, an avipox virus, a canarypox virus, a racoonpox and a swinepox virus, and the like. The vector-based compositions can comprise a vector that contains and expresses an ORF selected from the group consisting of ORFs 1 to 13, such as an ORF selected from ORFs 4, 7, 10 and 13; preferably ORFs 4 and/or 13, of a PCV-2, advantageously of any one of the PCV-2 strains identified herein. And, the immunogen in compositions (either PCV-2 and/or from another pig pathogen) can be recombinantly produced. The word plasmid is intended to include any DNA transcription unit in the form of a polynucleotide sequence comprising the PCV sequence to be expressed. Advantageously, the plasmid includes elements necessary for its expression; for instance, expression in vivo. The circular plasmid form, supercoiled or otherwise, is advantageous; and, the linear form is also included within the scope of the invention. The plasmid immunogenic or vaccine composition can be administered by way of a gene gun, intradermally via an needleless injector, subcutaneously or intramuscularly, or by mucosal route, or by any other means that allows for expression in vivo, and advantageously an immunogenic or protective response.

It is noted that the expression product generated by vectors or recombinants in this invention optionally can also be isolated and/or purified from infected or transfected cells; for instance, to prepare compositions for administration to pigs; however, in certain instances, it may be advantageous not to isolate and/or purify an expression product from a cell; for instance, when the cell or portions thereof enhance the immunogenic effect of the polypeptide. And, techniques for protein purification and/or isolation from this disclosure and documents cited herein, inter alia, and thus within the ambit of the skilled artisan, can be used, without undue experimentation, to purify and/or isolate recombinant or vector expression products and/or subunits of PCV-2 and/or other pig pathogens, in the practice of the invention, and such techniques, in general, can include: precipitation by taking advantage of the solubility of the protein of interest at varying salt concentrations, precipitation with organic solvents, polymers and other materials, affinity precipitation and selective denaturation; column chromatography, including high performance liquid chromatography (HPLC), ion-exchange, affinity, immunoaffinity or dye-ligand chromatography; immunoprecipitation, gel filtration, electrophoretic methods, ultrafiltration and isoelectric focusing, and their combinations, inter alia.

The invention further envisages methods for the prevention and/or treatment of porcine circovirus-2 (PCV-2)-caused myocarditis, and/or abortion and/or intrauterine infection and/or post-weaning multisystemic wasting syndrome and/or other pathologic sequelae associated with PCV-2 comprising inducing an immunogenic or protective response against PCV-2 in a pig comprising administering to the pig an aforementioned or herein disclosed composition.

Thus, the invention comprehends a method for the prevention and/or treatment of porcine circovirus-2 (PCV-2)-caused myocarditis, and/or abortion and/or intrauterine infection and/or post-weaning multisystemic wasting syndrome and/or other pathologic sequelae associated with PCV-2 comprising inducing an immunogenic or protective response against PCV-2 in a pig comprising administering to the pig a composition comprising a pharmaceutically or veterinarily acceptable carrier or excipient or vehicle, with preferably an adjuvant, and an active agent comprising a PCV-2 immunogen. The method can be for the prevention of PCV-2-caused mycarditis and/or abortion and/or intrauterine infection comprising administering a composition comprising a pharmaceutically or veterinarily acceptable carrier and a PCV-2 immunogen. The PCV-2 immunogen can be an attenuated live whole PCV-2 or inactivated PCV-2. The method can involve a composition that is a subunit immunogenic, or vaccine composition. The method can involve the composition additionally including at least one immunogen from at least one additional pig pathogen, including a vector expressing such an immunogen or epitope; e.g., the at least one additional pig pathogen can be selected from the group consisting of PRRS, Mycoplasma hyopneumoniae, Actinobacillus pleuropneumoniae, E. coli, Pseudorabies, Hog cholera, Bordetella bronchiseptica, Pasteurella multocida, Erysipelothrix rhusiopathiae, Swine Influenza, and PPV and combinations thereof. The method can involve a vector that is a DNA vector plasmid, a bacteria such as an E. coli, a virus such as baculovirus, a herpesvirus including Aujeszky's disease virus, an adenovirus including a porcine adenovirus, a poxvirus, including a vaccinia virus, an avipox virus, a canarypox virus, and a swinepox virus, and the like. The method can involve a vector-based composition additionally including at least one sequence, fragment or epitope from at least one additional pig pathogen, or a vector expressing such a sequence, fragment or epitope, wherein the vector can also be the vector expressing the PCV-2 sequence, fragment or epitope. The method can involve a vector that contains and expresses an ORF selected from the group consisting of ORFs 1 to 13, e.g., an ORF selected from ORFs 4, 7, 10 and 13; preferably ORFs 4 and/or 13. The method can also involve an immunogen-based composition wherein one or more of the immunogen(s) is recombinantly produced. In this method, females and/or piglets are inoculated as described above.

In another embodiment, the invention involves a method for preparing any of the aforementioned or herein disclosed compositions comprising admixing the pharmaceutically or veterinarily acceptable carrier and the PCV-2 immunogen. The method can further include transfecting or infecting a cell or host with a recombinant vector that contains DNA encoding a PCV-2 immunogen and expresses that immunogen; and optionally purifying and/or isolating the immunogen from the cell. Similarly the method can include isolating and/or purifying a PCV-2 immunogen from PCV-2, or isolating PCV-2 from a sample.

The invention also provides a kit for preparing any of the aforementioned or herein disclosed compositions or for performing any of the aforementioned or herein disclosed methods comprising in a first container the pharmaceutically or veterinarily acceptable carrier or vehicle or excipient and in a second container the active agent comprising the PCV-2 immunogen, wherein the first and second containers are optionally packaged together, and the kit optionally includes instructions for admixture of ingredients of the composition and/or administration of the composition.

In yet another embodiment, the invention provides for administering any of the aforementioned or herein disclosed compositions to male and/or female pigs; to prevent transmission of PCV-2 and prevent or treat or control myocarditis and/or abortion and/or intrauterine infection associated with porcine circovirus-2, as well as post-weaning multisystemic wasting syndrome and other pathologic sequelae associated with PCV-2. Administration is preferably done as described above.

The term "comprising" in this disclosure can mean "including" or can have the meaning commonly given to the term "comprising" in U.S. Patent Law.

Other aspects of the invention are described in or are obvious from (and within the ambit of the invention) the following disclosure.

BRIEF DESCRIPTION OF DRAWINGS

FIG. 1 depicts SEQ ID No. 1, the PCV DNA sequence of the genome of the Imp. 1011–48121 strain.

FIG. 2 depicts SEQ ID No. 2, the DNA sequence of the genome of the Imp. 1011–48285 strain.

FIG. 3 depicts SEQ ID No. 3, the DNA sequence of the genome of the Imp. 999 strain.

FIG. 4 depicts SEQ ID No. 4, the DNA sequence of the genome of the Imp. 1010 strain.

FIG. 5 depicts SEQ ID No. 5, the DNA sequence of the genome of the PK/15 strain.

FIG. 6 depicts SEQ ID No. 6, the DNA sequence of the genome of the Imp. 999 strain as defined in the first filing in France on Oct. 3, 1997.

FIG. 7 depicts SEQ ID No. 7, the DNA sequence of the genome of the 1103 strain, isolated in Alberta, Canada. k means g (G) or t (T), y means c (C) or t (T). These variations of sequence were observed in the viral population.

FIG. 8 depicts SEQ ID No. 8, the DNA sequence of the genome of the 1121 strain, isolated in Saskatoon, Canada.

DETAILED DESCRIPTION

Porcine circovirus-2 (PCV-2) is an agent associated with post-weaning multisystemic wasting syndrome (PMWS) in swine populations. As shown in Examples 1 and 2, the potential spectrum of disease associated with PCV-2 is expanded by evidence of vertical transmission and associated reproductive failure.

In particular, Example 1 shows that PCV-2 was isolated from a litter of aborted piglets from a farm experiencing late term abortions and stillbirths. Severe, diffuse myocarditis was present in one piglet associated with extensive immunohistochemical staining for PCV-2 antigen. Variable amounts of PCV-2 antigen were also present in liver, lung and kidney of multiple fetuses. The presence of other agents that have been associated with fetal lesions and abortion in swine including porcine parvovirus, porcine reproductive respiratory syndrome virus, encephalomyocarditis virus and enterovirus could not be established.

More in particular, Example 2 shows that tissues obtained from 30 high health herds over a four-year period, and tested in routine cases of abortion or reproductive failure, were positive for PCV-2 in two submissions involving several stillborn piglets and non-viable neonates presenting with severe diffuse myocarditis, cardiac hypertrophy and evidence of chronic passive congestion. The two positive submissions were from the same farm, but occurred at two different times. The presence of PCV-2 in the hearts and other tissues of affected piglets was confirmed by immunohistochemistry and virus isolation. Failure to detect porcine circoviruses in cases of reproductive failure prior to 1999 in areas of endemic infections supports the view that reproductive disease is a new clinical manifestation of PCV-2 infection, and further suggests that sexual, as well as vertical, modes of transmission are responsible for viral dissemination in the pig population.

Accordingly, inoculation of pigs, e.g., female pigs, such as sows or gilts, with a composition including at least one PCV-2 immunogen (e.g. from at least one strain chosen among strains Imp1008, Imp1010, Imp999, Imp1011–48285, Imp1011–48121, 1103 and 1121) (which composition can also include at least one immunogen from at least one other porcine pathogen such as at least one porcine parvovirus, wherein when a vector is used the vector can co-express both the PCV-2 immunogen(s) and the at least one immunogen of the at least one other porcine pathogen, e.g., PPV immunogen(s), inter alia), in a schedule of immunization as described above, can prevent myocarditis and/or abortion and/or intrauterine infection associated with PCV-2, as well as post-weaning multisystemic wasting syndrome and other pathologic sequelae associated with PCV-2.

Thus, the invention involves methods and compositions using PCV-2 immunogen for preventing myocarditis and/or abortion and/or intrauterine infection associated with porcine circovirus-2, as well as post-weaning multisystemic wasting syndrome and other pathologic sequelae associated with PCV-2. In particular, immunogen from strain 1103 and/or strain 1121 is useful for methods and compositions using PCV-2 immunogen for preventing myocarditis and/or abortion and/or intrauterine infection associated with porcine circovirus-2

The PCV-2 immunogen can be any PCV-2 immunogen including any PCV-2-expressing vector identified in any herein cited document (or any document cited in herein cited documents) including any or all of: U.S. application Ser. No. 09/347,594, filed Jul. 1, 1999; French application No. 98 08777, filed Jul. 6, 1998; U.S. application Ser. No. 09/161, 092, filed Sep. 25, 1998; U.S. application Ser. No. 09/082, 558, filed May 21, 1998; French applications Nos. 97 12382, 98 00873 and 98 03707, filed Oct. 3, 1997, Jan. 22, 1998 and Mar. 20, 1998, respectively; WO-A-99 18214; the U.S. applications of Audonnet et al. and Bublot et al., Ser. Nos. 60/138,352 and 60/138,478, respectively, both filed Jun. 10, 1999 ("DNA VACCINE-PCV", and "PORCINE CIRCOVIRUS RECOMBINANT POXVIRUS VACCINE", respectively); and WO99/29717 (all of which and documents cited therein and in the prosecution thereof being hereby incorporated herein by reference). Thus, the immunogen from PCV-2 including a vector expressing such an immunogen can be prepared in accordance with herein cited documents (or documents cited in herein cited documents).

The composition comprising the PCV-2 immunogen employed in the practice of this invention can be as in any herein cited document (or any document cited in herein cited documents) including any or all of: U.S. application Ser. No. 09/347,594, filed Jul. 1, 1999; French application No. 98 08777, filed Jul. 6, 1998; U.S. application Ser. No. 09/161, 092, filed Sep. 25, 1998; U.S. application Ser. No. 09/082, 558, filed May 21, 1998; French applications Nos. 97 12382, 98 00873 and 98 03707, filed Oct. 3, 1997, Jan. 22, 1998 and Mar. 20, 1998, respectively; WO-A-99 18214; the U.S. applications of Audonnet et al. and Bublot et al., Ser. Nos. 60/138,352 and 60/138,478, respectively, both filed Jun. 10, 1999, and Ser. Nos. 09/586,535 and 09/583,545, filed May 31 and Jun. 1, 2000, respectively ("DNA VACCINE-PCV", and "PORCINE CIRCOVIRUS RECOMBINANT POXVIRUS VACCINE", respectively); and WO99/29717 (all of which and documents cited therein and in the prosecution thereof being hereby incorporated herein by reference). Thus, the composition comprising the PCV-2 immunogen including the vector expressing PCV-2 immunogen can be prepared as in herein cited documents.

The at least one immunogen from at least one other porcine pathogen can be as described in any of the aforementioned or herein cited patent or literature publications (or documents cited therein), or as used in known porcine vaccines or immunogenic compositions, or as in WO 98/03658, published Jan. 29, 1998 from PCT/FR97/01313, filed Jul. 15, 1997; or French application 96 09338, filed Jul. 19, 1996; or U.S. application Ser. No. 09/232,468, filed Jan. 15, 1999 for ("POLYNUCLEOTIDE VACCINE FORMULA AGAINST PORCINE REPRODUCTIVE AND RESPIRATORY PATHOLOGIES").

The amount of PCV-2 immunogen in compositions employed in the invention can be as described in any of the aforementioned or herein cited patent or literature publications (or documents cited therein). And, the amount of at least one immunogen from at least one other porcine pathogen can be as described in any of the aforementioned or herein patent or literature publications (or documents cited therein), or as used in known porcine vaccines or immunogenic compositions.

Compositions for use in the invention can be prepared in accordance with standard techniques well known to those skilled in the veterinary or pharmaceutical or arts. Such compositions can be administered in dosages and by techniques well known to those skilled in the veterinary arts taking into consideration such factors as the age, sex, weight, condition and particular treatment of the pig, and the route of administration. The compositions can be administered alone, or can be co-administered or sequentially administered with other compositions of the invention (e.g., other compositions comprising a PCV-2 immunogen) or with other prophylactic or therapeutic compositions (e.g., other porcine immunogenic or vaccine compositions). Thus, the invention also provides multivalent or "cocktail" or combination compositions and methods employing them. In this regard, reference is made to U.S. Pat. No. 5,843,456, incorporated herein by reference, and directed to rabies compositions and combination compositions and uses thereof.

Compositions of the invention may be used for parenteral or mucosal administration, preferably by intradermal or intramuscular routes. In particular for intradermal route, injection can be done using a needleless injector. When mucosal administration is used, it is possible to use oral, nasal, or ocular routes.

In such compositions the immunogen(s) may be in a mixture with a suitable carrier, diluent, or excipient such as sterile water, physiological saline, glucose or the like, and/or preferably with an adjuvant. The compositions can also be lyophilized or frozen. The compositions can contain auxiliary substances such as pH buffering agents, adjuvants, preservatives, polymer excipients used for mucosal routes, and the like, depending upon the route of administration and the preparation desired.

Standard texts, such as "REMINGTON'S PHARMACEUTICAL SCIENCE", 17th edition, 1985, incorporated herein by reference, may be consulted to prepare suitable preparations, without undue experimentation. Suitable dosages can also be based upon the text herein and documents cited herein.

Adjuvants are substances that enhance the immune response to immunogens. Adjuvants, can include aluminum hydroxide and aluminum phosphate, saponins e.g., Quil A, water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di(caprylate/caprate), glyceryl tri (caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycerol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic® products, especially L121. See Hunter et al., The Theory and Practical Application of Adjuvants (Ed. Stewart-Tull, D. E. S.). John Wiley and Sons, NY, pp 51–94 (1995) and Todd et al., Vaccine 15:564–570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

For example the adjuvant-containing vaccine is prepared in the following way: 67% v/v of aqueous phase comprising the immunogen are emulsified in 2.3% w/v of anhydromannitol oleate, 2.6% w/v of oleic acid ethoxylated with 11 EO (ethylene oxide) and 28.1% v/v of light liquid paraffin oil (European Pharmacopea type) with the aid of an emulsifying turbomixer.

An alternative method for preparing the emulsion consists in emulsifying, by passages through a high-pressure homogenizer, a mixture of 5% w/v squalane, 2.5% w/v Pluronic®, L121, 0.2% w/v of an ester of oleic acid and of anhydrosorbitol ethoxylated with 20 EO, 92.3% v/v of the aqueous phase comprising the immunogen.

It is also possible to formulate with synthetic polymers (e.g., homo- and copolymers of lactic and glycolic acid, which have been used to produce microspheres that encapsulate immunogens, see Eldridge et al., Mol. Immunol. 28:287–294 (1993), e.g., biodegradable microspheres), with cytokines such as IL-2 and IL-12 (see, e.g., U.S. Pat. No. 5,334,379), and GMCSF, advantageously porcine GMCSF (granulocyte macrophage-colony stimulating factor; see, generally, U.S. Pat. Nos. 4,999,291 and 5,461,663, see also Clark et al., Science 1987, 230:1229; Grant et al., Drugs, 1992, 53:516), inter alia. Certain adjuvants can be expressed in vivo with immunogen(s) and/or epitope(s); e.g., cytokines, GMCSF (see, e.g., Inumaru and Takamatsu, Immunol. Cell. Biol., 1995, 73:474–76 concerning a plasmid encoding and expressing porcine GM-CSF).

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 (incorporated herein by reference) which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are cross-linked with an allyl sucrose or with allyl pentaerythritol. Among then, there may be mentioned Carbopol® 974P, 934P and 971P. Among the copolymers of maleic anhydride and alkenyl derivative, the copolymers EMA® (Monsanto) which are copolymers of maleic anhydride and ethylene, linear or cross-linked, for example cross-linked with divinyl ether, are preferred. Reference may be made to J. Fields et al., Nature, 186 : 778–780, 4 Jun. 1960, incorporated herein by reference.

From the point of view of their structure, the polymers of acrylic or methacrylic acid and the copolymers EMA® are preferably formed of basic units of the following formula:

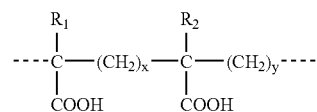

in which:

$R_1$ and $R_2$, which are identical or different, represent H or $CH_3$;

x=0 or 1, preferably x=1; and y=1 or 2, with x+y=2.

For the copolymers EMA®, x=0 and y=2. For the carbomers, x=y=1.

The dissolution of these polymers in water leads to an acid solution that will be neutralized, preferably to physiological pH, in order to give the adjuvant solution into which the immunogenic, immunological or vaccine composition itself will be incorporated. The carboxyl groups of the polymer are then partly in COO⁻ form.

Preferably, a solution of adjuvant according to the invention, especially of carbomer, is prepared in distilled water, preferably in the presence of sodium chloride, the solution obtained being at acidic pH. This stock solution is diluted by adding it to the desired quantity (for obtaining the desired final concentration), or a substantial part thereof, of water charged with NaCl, preferably physiological saline (NaCL 9 g/l) all at once in several portions with concomitant or subsequent neutralization (pH 7.3 to 7.4), preferably with NaOH. This solution at physiological pH will be used as it is for mixing with the vaccine, which may be especially stored in freeze-dried, liquid or frozen form.

The polymer concentration in the final vaccine composition can be 0.01% to 2% w/v, e.g., 0.06 to 1% w/v, such as 0.1 to 0.6% w/v.

From this disclosure and the knowledge in the art, the skilled artisan can select a suitable adjuvant, if desired, and the amount thereof to employ in an immunological, immunogenic or vaccine composition according to the invention, without undue experimentation.

The immunogenic or vaccine compositions according to the invention may be associated to at least one live attenuated, inactivated, or sub-unit vaccine, or recombinant vaccine (e.g. poxvirus as vector or DNA plasmid) expressing at least one immunogen or epitope of interest from at least one another pig pathogen.

Compositions in forms for various administration routes are envisioned by the invention. And again, the effective dosage and route of administration are determined by known factors, such as age, sex, weight and other screening procedures which are known and do not require undue experimentation. Dosages of each active agent can be as in herein cited documents and/or can range from one or a few to a few hundred or thousand micrograms, e.g., 1 µg to 1 mg, for a subunit immunogenic, or vaccine composition; and, $10^4$ to $10^{10}$ TCID$_{50}$ advantageously $10^6$ to $10^8$ TCID$_{50}$ for an inactivated (titre before inactivation) immunogenic, or vaccine composition. For a live attenuated immunogenic or vaccine composition, the dose can be between $10^1$ and $10^8$ TCID$_{50}$ advantageously $10^3$ and $10^6$ TCID$_{50}$.

Recombinants or vectors can be administered in a suitable amount to obtain in vivo expression corresponding to the dosages described herein and/or in herein cited documents. For instance, suitable ranges for viral suspensions can be determined empiracally. The viral vector or recombinant in the invention can be administered to a pig or infected or transfected into cells in an amount of about at least $10^3$ pfu; more preferably about $10^4$ pfu to about $10^{10}$ pfu, e.g., about $10^5$ pfu to about $10^9$ pfu, for instance about $10^6$ pfu to about $10^8$ pfu, per dose, e.g. of about 2 ml. And, if more than one gene product is expressed by more than one recombinant, each recombinant can be administered in these amounts; or, each recombinant can be administered such that there is, in combination, a sum of recombinants comprising these amounts.

In plasmid compositions employed in the invention, dosages can be as described in documents cited herein or as described herein. For instance, suitable quantities of each plasmid DNA in plasmid compositions can be 1 µg to 2 mg, preferably 50 µg to 1 mg. Documents cited herein regarding DNA plasmid vectors may be consulted by the skilled artisan to ascertain other suitable dosages for DNA plasmid vector compositions of the invention, without undue experimentation.

However, the dosage of the composition(s), concentration of components therein and timing of administering the composition(s), which elicit a suitable immunologic response, can be determined by methods such as by antibody titrations of sera, e.g., by ELISA and/or seroneutralization assay analysis and/or by vaccination challenge evaluation in pig. Such determinations do not require undue experimentation from the knowledge of the skilled artisan, this disclosure and the documents cited herein. And, the time for sequential administrations can be likewise ascertained with methods ascertainable from this disclosure, and the knowledge in the art, without undue experimentation.

The PCV-2 immunogen can be obtained from PCV-2 or can be obtained from in vitro recombinant expression of PCV-2 gene(s) or portions or epitopes thereof. Methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 5,756,103, 5,766,599, 6,004,777, 5,990,091, 6,033,904, 5,869,312, 5,382,425, PCT publications WO 94/16716, WO 96/39491, WO 95/30018, Paoletti, "Applications of pox virus vectors to vaccination: An update," PNAS USA 93:11349–11353, October 1996, Moss, "Genetically engineered poxviruses for recombinant gene expression, vaccination, and safety," PNAS USA 93:11341–11348, October 1996, Smith et al., U.S. Pat. No. 4,745,051 (recombinant baculovirus), Richardson, C. D. (Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, December, 1983, Vol. 3, No. 12, p. 2156–2165; Pennock et al., "Strong and Regulated Expression of *Escherichia coli* B-Galactosidase in Infect Cells with a Baculovirus vector," Molecular and Cellular Biology March 1984, Vol. 4, No. 3, p. 399–406; EPA 0 370 573, U.S. application Ser. No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93:11307–11312, October 1996, Andreansky et al., "The application of genetically engineered herpes simplex viruses to the treatment of experimental brain tumors," PNAS USA 93:11313–11318, October 1996, Robertson et al. "Epstein-Barr virus vectors for gene delivery to B lymphocytes," PNAS USA 93:11334–11340, October 1996, Frolov et al., "Alphavirus-based expression vectors: Strategies and applications," PNAS USA 93:11371–11377, October 1996, Kitson et al., J. Virol. 65, 3068–3075, 1991; U.S. Pat. Nos. 5,591,439, 5,552,143, WO 98/00166, allowed U.S. application Ser. Nos. 08/675,556, and 08/675,566 both filed Jul. 3, 1996 (recombinant adenovirus), Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, PCT WO91/11525, Felgner et al. (1994), J. Biol. Chem. 269, 2550–2561, Science, 259: 1745–49, 1993 and McClements et al., "Immunization with DNA vaccines encoding glycoprotein D or glycoprotein B, alone or in combination, induces protective immunity in animal models of herpes simplex virus-2 disease," PNAS USA 93:11414–11420, October 1996, and U.S. Pat. Nos. 5,591,639, 5,589,466, and 5,580,859 relating to DNA expression vectors, inter alia. See also WO 98/33510; Ju et al., Diabetologia, 41:736–739, 1998 (lentiviral expression system); Sanford et al., U.S. Pat. No. 4,945,050; Fischbach et al. (Intracel), WO 90/01543; Robinson et al., seminars in IMMUNOLOGY, vol. 9, pp. 271–283 (1997) (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery), as well as other documents cited herein. A viral vector, for instance, selected from pig herpes viruses, such as Aujeszky's disease virus, porcine adenovirus, poxviruses, especially vaccinia virus, avipox virus, canarypox virus, and swinepox virus, as well as DNA vectors (DNA plasmids) are advantageously employed in the practice of the invention.

The expression product from the PCV-2 gene(s) or portions thereof can be useful for generating antibodies such as monoclonal or polyclonal antibodies that are useful for diagnostic purposes. Similarly, expression product(s) from the PCV-2 gene(s) or portions thereof can be useful in diagnostic applications.

Further, one skilled in the art can determine an epitope of interest in a PCV-2 immunogen, or in an immunogen of another porcine pathogen, without undue experimentation, from the disclosure herein and the knowledge in the art; see, e.g., WO 98/40500, incorporated herein by reference, regarding general information for determining an epitope of interest or an epitopic region of a protein, inter alia.

With particular reference to U.S. application Ser. No. 09/161,092, filed Sep. 25, 1998, U.S. application Ser. No. 09/082,558, filed May 21, 1998, French applications Nos. 97 12382, 98 00873 and 98 03707, filed Oct. 3, 1997, Jan. 22, 1998 and Mar. 20, 1998, respectively, and, WO-A-99 18214 (all incorporated herein by reference), particularly advantageous immunogenic, immunological or vaccine compositions are: An immunogenic or vaccine composition, collected from a cell culture in vitro which has been infected with a purified preparation of PCV-2, such as a purified preparation of porcine circovirus selected from the group consisting of the preparations deposited at the ECACC, under the following references: accession No. V97100219 (strain Imp.1008), No. V97100218 (strain Imp.1010) and accession No. V97100217 (strain Imp.999) deposited Oct. 2, 1997, accession No. V98011608 (strain Imp.1011–48285) and No. V98011609 (strain Imp.1011–48121) deposited Jan. 16, 1998, accession No. 00012710 (strain 1103) and No. 00012709 (strain 1121) deposited Feb. 2, 2000, or an immunogenic or vaccine composition comprised of porcine circovirus produced on, and isolated from cell culture in vitro, these cells having been infected with a porcine circovirus capable of being isolated from a physiological sample or from a tissue sample, especially lesions, from a pig having the PMWS syndrome, e.g., such a composition wherein the porcine circovirus is produced on, and isolated from a pig kidney cell line, for instance, produced on, and isolated from PK/15 cells free from contamination with PCV-1; or such a composition comprising or prepared from a culture extract or supernatant, collected from a cell culture in vitro which have been infected with a such a circovirus. Thus, porcine circovirus can be an immunogen. For instance, the vaccine or immunogenic composition can comprise the attenuated live whole immunogen (e.g., virus), advantageously, in a veterinarily or pharmaceutically acceptable vehicle or diluent and optionally an a veterinarily or pharmaceutically acceptable adjuvant, as well as, optionally, a freeze-drying stabilizer. The immunogen (e.g., virus) can be inactivated and the vaccine or immunogenic composition can additional and/or optionally comprise, a veterinarily or pharmaceutically acceptable vehicle or diluent and optionally a veterinarily or pharmaceutically acceptable adjuvant. The vaccine or immunogenic composition can comprise PCV-2 immunogens and/or immunogens of several porcine circoviruses (including PCV-2 or several strains of PCV-2, and including PCV-1), as well as optionally additionally immunogens from another pig pathogen; e,g, PRRS, *Mycoplasma hyopneumoniae, Actinobacillus pleuropneumoniae, E. coli*, Pseudorabies, Hog cholera, *Bordetella bronchiseptica, Pasteurella multocida, Erysipelothrix rhusiopathiae*, Swine Influenza, PPV (see also U.S. application Ser. No. 09/347,594, filed Jul. 1, 1999 and French application No. 98 08777, filed Jul. 6, 1998).

For the production of circovirus antigenic preparations, the circoviruses may be obtained after passage on cells, in particular cell lines, e.g. PK/15 cells. The culture supernatants or extracts, optionally purified by standard techniques, may be used.

In the context of attenuated PCV, the attenuation may be carried out according to the customary methods, e.g. by passage on cells, preferably by passage on pig cells, especially cell lines, such as PK/15 cells (for example from 20 to 150, especially of the order of 40 to 100, passages).

In the context of inactivated vaccine, the PCV, with the fractions which may be present, is inactivated according to techniques known to persons skilled in the art. The inactivation will be preferably carried out by the chemical route, e.g. by exposing the antigen to a chemical agent such as formaldehyde (formalin), paraformaldehyde, β-propiolactone or ethyleneimine or its derivatives, and/or by physical treatment. The preferred method of inactivation will be herein the exposure to a chemical agent and in particular to ethyleneimine or to β-propiolactone.

The immunogen in the vaccine or immunogenic composition can be expressed from a DNA fragment containing a sequence or fragment thereof (advantageously encoding at least one epitope) selected from the group consisting of the sequences designated by the references SEQ ID No: 1, SEQ ID No: 2, SEQ ID No: 3, SEQ ID No: 4, SEQ ID No: 6 (in U.S. application Ser. No. 09/161,092, filed Sep. 25, 1998, U.S. application Ser. No. 09/082,558, filed May 21, 1998, French applications Nos. 97 12382, 98 00873 and 98 03707, filed Oct. 3, 1997, Jan. 22, 1998 and Mar. 20, 1998, respectively, and, WO-A-99 18214), as well as SEQ ID No: 7 and SEQ ID No: 8 (FIGS. 1–8). The immunogen in the vaccine or immunogenic composition can be expressed from a DNA fragment containing an ORF selected from the group consisting of ORFs 1 to 13, such as ORFs 4, 7, 10 and 13; preferably ORFs 4 and/or 13, of a PCV-2 strain, in particular of any one of the above identified strains (as designated in U.S. application Ser. No. 09/161,092, filed Sep. 25, 1998, U.S. application Ser. No. 09/082,558, filed May 21, 1998, French applications Nos. 97 12382, 98 00873 and 98 03707, filed Oct. 3, 1997, Jan. 22, 1998 and Mar. 20, 1998, respectively, and, WO-A-99 18214). Thus, the immunogen or a portion thereof, such as an epitope of interest can be obtained by in vitro expression thereof from a recombinant or a vector. The immunogen may be further purified and/or concentrated by the conventional methods.

The immunogen in the vaccine or immunogenic composition can be expressed in vivo by an expression vector comprising a DNA fragment containing a sequence or fragment thereof (advantageously encoding at least one epitope) selected from the group consisting of the sequences designated by the references SEQ ID No: 1, SEQ ID No: 2, SEQ ID No: 3, SEQ ID No: 4, SEQ ID No: 6 (in U.S. application Ser. No. 09/161,092, filed Sep. 25, 1998, U.S. application Ser. No. 09/082,558, filed May 21, 1998, French applications Nos. 97 12382, 98 00873 and 98 03707, filed Oct. 3, 1997, Jan. 22, 1998 and Mar. 20, 1998, respectively, and, WO-A-99 18214), as well as SEQ ID No: 7 and SEQ ID No: 8 (FIGS. 1–8). Similarly, the immunogen in the vaccine, immunogenic or immunological composition can be expressed in vivo by an expression vector comprising a DNA fragment containing an ORF selected from the group consisting of ORFs 1 to 13, such as ORFs 4, 7, 10 and 13; preferably ORFs 4 and/or 13, of a PCV-2 strain, in particular of any one of the above identified strains (as designated in U.S. application Ser. No. 09/161,092, filed Sep. 25, 1998, U.S. application Ser. No. 09/082,558, filed May 21, 1998, French applications Nos. 97 12382, 98 00873 and 98 03707, filed Oct. 3, 1997, Jan. 22, 1998 and Mar. 20, 1998, respectively, and, WO-A-99 18214). That is, the vaccine or immunogenic composition can comprise and expression vector that expresses the immunogen or a portion thereof, e.g., an epitope of interest, in vivo.

The expression vector can be any suitable vector such as a vector selected from DNA plasmids, bacteria such as *E. coli*, viruses such as baculovirus, herpesvirus such as Aujeszky's disease virus, adenovirus including porcine adenovirus, poxviruses, especially vaccinia virus, avipox virus, canarypox virus, and swinepox virus, inter alia (See also the U.S. applications of Audonnet et al. and Bublot et al., Ser. Nos. 60/138,352 and 60/138,478, respectively, both filed Jun. 10, 1999 ("DNA VACCINE-PCV", and "PORCINE CIRCOVIRUS RECOMBINANT POXVIRUS VACCINE", respectively).

Accordingly, the invention also comprehends nucleic acid molecules and vectors containing them, as well as expression products therefrom, compositions comprising such nucleic acid molecules and/or vectors and/or expression products, as well as methods for making and using any or all of these embodiments. The invention especially encompasses herein disclosed nucleic acid molecules, nucleic acid molecules of documents cited or referenced herein, including PCT WO 99/29717, fragments thereof, e.g., ORFs and/or fragments encoding an immunogen or epitope, as well as nucleic acid molecules of strains 1103 and/or 1121, and fragments thereof, as well as vectors comprising these nucleic acid molecules, compositions comprising these nucleic molecules, vectors, or expression products therefrom, compositions comprising such expression products, primers or probes for such nucleic acid molecules, and uses or methods involving these embodiments, e.g., for detecting, diagnosing, assaying for PCV-2, for inducing an immunologenic or protective response, and the like. Indeed, this invention encompasses any inventions disclosed and/or claimed in PCT WO 99/29717 or any National application claiming priority therefrom or from the U.S. Provisionals from which that PCT claims priority.

As earlier mentioned, embodiments of the invention can include antibodies. Such antibodies can be polyclonal or monoclonal antibodies; for instance, prepared from the aforementioned circovirus, or from a polypeptide encoded by a DNA fragment having a sequence selected from the group consisting of SEQ ID NOS. 1, 2, 3, 4, 6, 7 and 8, (FIGS. 1–8) or from a polypeptide from expression by a vector comprising a sequence selected from the group consisting of SEQ ID NOS. 1, 2, 3, 4, 6, 7 and 8; or from a polypeptide from expression by a vector comprising DNA including an ORF selected from the group consisting of ORFs 1 to 13 (as designated in U.S. application Ser. No. 09/161,092, filed Sep. 25, 1998, U.S. application Ser. No. 09/082,558, filed May 21, 1998, French applications Nos. 97 12382, 98 00873 and 98 03707, filed Oct. 3, 1997, Jan. 22, 1998 and Mar. 20, 1998, respectively, and, WO-A-99 18214). The skilled artisan may use techniques known in the art to elicit antibodies and to generate monoclonal or polyclonal antibodies. Antibodies and antigens can be used in diagnostics.

U.S. application Ser. No. 09/161,092, filed Sep. 25, 1998, U.S. application Ser. No. 09/082,558, filed May 21, 1998, French applications Nos. 97 12382, 98 00873 and 98 03707, filed Oct. 3, 1997, Jan. 22, 1998 and Mar. 20, 1998, respectively, and, WO-A-99 18214 also provide for probes or primers which can be useful, for instance, in detecting PCV-2 DNA, as well as for amplifying PCV-2 DNA, e.g., for preparing an expression vector. A probe or primer can be any stretch of at least 8, preferably at least 10, more preferably at least 12, 13, 14, or 15, such as at least 20, e.g., at least 23 or 25, for instance at least 27 or 30 nucleotides in PCV-2 genome or a PCV-2 gene which are unique to PCV-2 or which are in PCV-2 and are least conserved among the PCV or circovirus family. As to PCR or hybridization primers or probes and optimal lengths therefor, reference is also made to Kajimura et al., GATA 7(4):71–79 (1990). Hybridization is advantageously under conditions of high stringency, as the term "high stringency" would be understood by those with skill in the art (see, for example, Sambrook et al., 1989, Molecular Cloning: A Laboratory Manual, Cold Spring Harbor Laboratory Press, Cold Spring Harbor, N.Y. and Hames and Higgins, eds., 1985, Nucleic Acid Hybridization, IRL Press, Oxford, U.K.). Hybridization will be understood to be accomplished using well-established techniques, including but not limited to Southern blot hybridization, Northern blot hybridization, in situ hybridization and, advantageously, Southern hybridization to PCR-amplified DNA fragments.

Like probes or primers, peptides which are not full-length PCV-2 proteins are part of invention and can be any stretch of at least 8, preferably at least 10, more preferably at least 12, 13, 14, or 15, such as at least 20, e.g., at least 23 or 25, for instance at least 27 or 30 amino acids in PCV-2 which are unique to PCV-2 or which are in PCV-2 and are least conserved among the PCV and/or circovirus family. Alternatively or additionally, the amino acids of the invention which are not full length PCV-2 proteins can be an epitopic region of a PCV-2 protein.

And, as to DNA and protein sequences used in the invention, they can have homology, identity or similarity and degrees thereof as defined in U.S. application Ser. No. 09/347,594, filed Jul. 1, 1999 with homology, identity or similarity advantageously determined as discussed in U.S. Ser. No. 09/347,594.

The PCV-2 sequences derived from Meehan et al., 1998 (Strain Imp.1010; ORF1 nucleotides 398–1342; ORF2 nucleotides 1381–314; and correspond respectively to ORF4 and ORF13 in U.S. application Ser. No. 09/161,092 of 25 Sep. 1998 and to COL4 and COL13 in WO-A-9918214). Several PCV-2 strains and their sequences are disclosed herein and called Imp1008, Imp999, Imp1011–48285, Imp1011–48121, 1103 and 1121. Other strains are disclosed in A. L. Hamel et al. J. Virol. June 1998, vol 72, 6: 5262–5267 (GenBank AF027217) and in I. Morozov et al. J. Clinical Microb. September 1998 vol. 36, 9: 2535–2541, as well as GenBank AF086834, AF086835 and AF086836. These sequences, or ORFs therefrom, or regions thereof encoding an antigen or immunogen or epitope of interest can also be used in the practice of this invention.

The invention also encompasses the equivalent sequences to those used or mentioned herein and in documents cited herein; for instance, sequences that are capable of hybridizing to the nucleotide sequence under high stringency conditions (see, e.g., Sambrook et al. (1989). Among the equivalent sequences, there may also be mentioned the gene fragments conserving the immunogenicity of the complete sequence, e.g., an epitope of interest.

The homology between the whole genome of PCV types 1 and 2 is about 75%. But within type 2, homology is generally above 95%. Thus, in the practice of the invention, use of any PCV-2 strain is encompassed by equivalence. A criteria can be that the strain is of type 2, e.g. that homology at the nucleotide level of the whole genome is equal or greater than 85%, advantageously 90% or greater, more advantageously 95% or greater, preferably 97, 98 or 99% or greater, with the strains disclosed herein, e.g. strain Imp1010.

Limits of the ORFs of strain Imp1010 are given in the following Table 1:

| Name | Start | End | Strand | Size of the ORF (nucleotides (nt)) | Protein size (amino acids (aa)) |
|---|---|---|---|---|---|
| ORF1 | 103 | 210 | Sense | 108 nt | 35 aa |
| ORF2 | 1180 | 1317 | Sense | 138 nt | 45 aa |
| ORF3 | 1363 | 1524 | Sense | 162 nt | 53 aa |
| ORF4 | 398 | 1342 | Sense | 945 nt | 314 aa |
| ORF5 | 900 | 1079 | Sense | 180 nt | 59 aa |
| ORF6 | 1254 | 1334 | Sense | 81 nt | 26 aa |
| ORF7 | 1018 | 704 | Antisense | 315 nt | 104 aa |
| ORF8 | 439 | 311 | Antisense | 129 nt | 42 aa |
| ORF9 | 190 | 101 | Antisense | 90 nt | 29 aa |
| ORF10 | 912 | 733 | Antisense | 180 nt | 59 aa |
| ORF11 | 645 | 565 | Antisense | 81 nt | 26 aa |
| ORF12 | 1100 | 1035 | Antisense | 66 nt | 21 aa |
| ORF13 | 314 | 1381 | Antisense | 702 nt | 213 aa |

The ORFs are defined with respect to strain Imp1010. The invention also encompasses the use of the corresponding ORFs in any other PCV-2 strain, and any of the PCV-2 strains as defined herein or in documents cited herein. Thus, from the genomic nucleotide sequence, it is routine art to determine the ORFs using a standard software, such as MacVector®. Also, alignment of genomes with that of strain 1010 and comparison with strain 1010 ORFs allows the one skilled in the art to readily determine the ORFs on the genome for another strain (e.g. those disclosed in WO-A-99 18214, say Imp 1008, Imp 1011–48121, Imp 1011–48285, Imp 999, as well as the new strains 1103 and 1121). Using software or making alignment is not undue experimentation and directly provides access to equivalent ORFs.

For example, referring to FIGS. 6 and 7, the corresponding ORFs of strains 1103 and 1121 are as given in the following Table 2:

| Name | Start | End | Strand | Size of the ORF (nucleotides (nt)) | Protein Size (amino acids (aa)) |
|---|---|---|---|---|---|
| ORF1 | 1524 | 1631 | Sense | 108 nt | 35 aa |
| ORF2 | 833 | 970 | Sense | 138 nt | 45 aa |
| ORF3 | 1016 | 1177 | Sense | 162 nt | 53 aa |

-continued

| Name | Start | End | Strand | Size of the ORF (nucleotides (nt)) | Protein Size (amino acids (aa)) |
|---|---|---|---|---|---|
| ORF4 | 51 | 995 | Sense | 945 nt | 314 aa |
| ORF5 | 553 | 732 | Sense | 180 nt | 59 aa |
| ORF6 | 907 | 987 | Sense | 81 nt | 26 aa |
| ORF7 | 671 | 357 | Antisense | 315 nt | 104 aa |
| ORF8 | 92 | 1732 | Antisense | 129 nt | 42 aa |
| ORF9 | 1611 | 1522 | Antisense | 90 nt | 29 aa |
| ORF10 | 565 | 386 | Antisense | 180 nt | 59 aa |
| ORF11 | 298 | 218 | Antisense | 81 nt | 26 aa |
| ORF12 | 753 | 688 | Antisense | 66 nt | 21 aa |
| ORF13 | 1735 | 1037 | Antisense | 702 nt | 213 aa |

Also equivalent and useful in the practice of the invention are the nucleotide sequences which change neither the functionality nor the strain specificity (say of strain type 2) of the gene considered or those of the polypeptides encoded by this gene. The sequences differing through the degeneracy of the code are, of course, be included in the practice of the invention.

For ORF4, homology between PCV-1 and PCV-2 is about 86%, and for ORF13, the homology between PCV-1 and PCV-2 is about 66%. Thus, also equivalent sequences useful in the practice of the present invention, for ORF4, are those sequences having an homology equal or greater than 88%, advantageously 90% or greater, preferably 92% or 95% or greater homology with ORF4 of strain Imp1010, and for ORF13, those sequences having an homology equal or greater than 80%, advantageously 85% or greater, preferably 90% or 95% or greater than ORF13 of strain Imp1010. (Using the terminology of U.S. application Ser. No. 09/161,092 of 25 Sep. 1998.)

For homology regarding the other ORFs, one can determine those sequences which come from a PCV strain having an ORF4 and/or an ORF13 which have an homology as defined above with the corresponding ORF of strain 1010. For ORF7, sequences useful in the practice of the invention include those sequences having an homology that is advantageously equal to or greater than 80%, more advantageously 85% or greater, preferably 90% or 95% or greater with ORF7 of strain Imp1010. For ORF10, sequences useful in the practice of the invention include those sequences having an homology that is advantageously equal to or greater than 86%, more advantageously 90% or greater, preferably 95% or greater with ORF10 of strain Imp1010. (Using the terminology of U.S. application Ser. No. 09/161,092 of 25 Sep. 1998.)

Also, equivalent sequences useful in the practice of this present invention, for ORF1 of Meehan et al., 1998, are those sequences having an homology equal or greater than 88%, advantageously 90% or greater, preferably 92% or 95% or greater with ORF1 of strain Imp1010, and for ORF2 of Meehan et al., 1998, are those sequences having an homology equal or greater than 80%, advantageously 85% or greater, preferably 90% or 95% or greater with ORF2 of strain Imp1010.

ORF1 and ORF2 according to Meehan et al., 1998 has the potential to encode proteins with predicted molecular weights of 37.7 kD and 27.8 kD respectively. ORF3 and ORF4 (according to Meehan et al. 1998, correspond to ORF7 and ORF10 respectively in WO-A-9918214 and/or U.S. application Ser. No. 09/161,092 of 25 Sep. 1998) has the potential to encode proteins with predicted molecular weights of 11.9 and 6.5 kD respectively. The sequence of these ORFs is also available in Genbank AF 055392. They can also be incorporated in plasmids and be used in accordance with the invention alone or in combination, e.g. with ORF1 and/or ORF2 of Meehan et al., 1998.

The other ORFs 1–3 and 5, 6, 8–9, 11–12 disclosed in U.S. application Ser. No. 09/161,092 of 25 Sep. 1998 (COLs 1–3 and 5, 6, 8–9, 11–12 in WO-A-9918214), or region(s) thereof encoding an antigen or epitope of interest, may be used in the practice of this invention, e.g., alone or in combination or otherwise with each other or with the ORFs 1 and/or 2 of Meehan et al., 1998 or region(s) thereof encoding antigen(s) or epitope(s). Similarly, for homology, one can determine that there are equivalent sequences which come from a PCV strain having an ORF2 and/or an ORF1 which have an homology as defined above with the corresponding ORF of strain 1010 as defined in Meehan et al., 1998. For ORF3 according to Meehan et al., 1998, an equivalent sequence has homology thereto that is advantageously, for instance, equal or greater than 80%, for example 85% or greater, preferably 90% or 95% or greater with ORF3 of strain Imp1010. And, for ORF4 according to Meehan et al., 1998, advantageously an equivalent sequence has homology that is equal or greater than 86%, advantageously 90% or greater, preferably than 95% or greater with ORF4 of strain Imp1010.

Nucleotide sequence homology can be determined using the "Align" program of Myers and Miller, ("Optimal Alignments in Linear Space", CABIOS 4, 11–17, 1988, incorporated herein by reference) and available at NCBI. Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman, 1983 PNAS USA 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence.

RNA sequences within the scope of the invention can be derived from DNA sequences, by thymidine (T) in the DNA sequence being considered equal to uracil (U) in RNA sequences.

Additionally or alternatively, amino acid sequence similarity or identity or homology can be determined using the BlastP program (Altschul et al., Nucl. Acids Res. 25, 3389–3402, incorporated herein by reference) and available at NCBI. The following references (each incorporated herein by reference) provide algorithms for comparing the relative identity or homology of amino acid residues of two proteins, and additionally or alternatively with respect to the foregoing, the teachings in these references can be used for determining percent homology or identity: Needleman S B and Wunsch C D, "A general method applicable to the search for similarities in the amino acid sequences of two proteins," *J. Mol. Biol.* 48:444–453 (1970); Smith T F and Waterman M S, "Comparison of Bio-sequences," *Advances in Applied Mathematics* 2:482–489 (1981); Smith T F, Waterman M S and Sadler J R, "Statistical characterization of nucleic acid sequence functional domains," *Nucleic Acids Res.*, 11:2205–2220 (1983); Feng D F and Dolittle R F, "Progressive sequence alignment as a prerequisite to correct phylogenetic trees," *J. of Molec. Evol.*, 25:351–360 (1987); Higgins D G and Sharp P M, "Fast and sensitive multiple sequence alignment on a microcomputer," *CABIOS*, 5:151–153 (1989); Thompson J D, Higgins D G and Gibson T J, "ClusterW: improving the sensitivity of progressive multiple sequence alignment through sequence weighing, positions-specific gap penalties and weight matrix choice, *Nucleic Acid Res.*, 22:4673–480 (1994); and, Devereux J, Haeberlie P and Smithies O, "A comprehensive set of sequence analysis program for the VAX," *Nucl. Acids Res.*, 12: 387–395 (1984).

The invention further comprehends uses of a PCV-2 immunogen, either alone or in further combination with an immunogen of another porcine pathogen to generate compositions according to the invention, e.g., admixing the ingredients; and, the invention also therefore comprehends kits wherein components are individually contained and optionally the containers are packaged together for admixture and/or administration, wherein the kit can also optionally include instructions for admixture and/or administration.

While the invention has been discussed in terms of administering to female pigs immunogenic or vaccine compositions comprising a PCV-2 immunogen, the invention can also comprehend administering such compositions to sow or gilt and/or to boar as described herein; Thus, both mother and offspring (e.g., sow, gilt) and boar can be administered compositions of the invention and/or can be the subject of performance of methods of the invention. Accordingly, populations of pigs can be administered compositions of the inventions and/or can be the subject of performance of methods of the invention.

According to the present invention, immunogenic and vaccine compositions may comprise immunogens from more than one PCV-2 strain. For example, it is possible to combine immunogens from strains 1121 and 1103, from one or both of these strains with at least one other strain disclosed herein, or any other combination.

The present invention provides for methods allowing the one skilled in the art to evaluate the efficacy of vaccines against PCV-2. A first method is an ELISA method or with seroneutralization. A second method is a vaccination followed by challenge with a virulent PCV-2 strain, e.g. one of the strains disclosed herein. In other words, the invention allows one to check for PCV immunogens, including PCV-1 immunogens able to elicit an immunologic or protective response against PCV-2.

Thus one aspect of the invention is to provide immunogenic or vaccinal compositions comprising a PCV immunogen and able to elicit an immunogenic or protective response against PCV-2. The invention relates also to methods of immunization or vaccination using such an immunogen, as well as to the use of such an immunogen to produce such an immunogenic or vaccinal composition.

The invention shall be further described by way of the following Example And Results, provided for illustration and not to be considered a limitation of the invention.

EXAMPLES

Example/Result 1

Myocarditis, Abortion and Intrauterine Infection Associated with PCV-2

Late term abortions and farrowings with both stillborn and mummified piglets occurred in a new 450-female pig swine facility as it was brought into production. Pseudopregnancy was also observed in several gilts. Gilts received two doses of an inactivated vaccine containing parvovirus and leptospiral immunogens prior to breeding.

A litter received for postmortem examination consisted of nine fetuses that appeared to have died at various stages of gestation. There were 2 mummified, 2 macerated, 3 autolysed and 2 fresh, stillborn piglets. Lesions were observed on gross pathological examination in one partially autolysed fetus only. In this fetus both ventricles of the heart were dilated, the liver was enlarged and firm and there was both hydrothorax and ascites. Histopathologically, there were extensive areas of myocardial degeneration or necrosis with edema and mild fibrosis, and a diffuse moderate-infiltration of lymphocytes and macrophages. There was marked generalized hepatic congestion and hepatocellular loss. The spleen and kidneys were also congested. Significant histological lesions were not detected in the other fetuses.

Immunohistochemical staining for PCV-2 was performed as previously described using a rabbit polyclonal antiserum and a monoclonal antibody that were raised against PCV-2, on sections of formalin-fixed, routinely processed and embedded tissue (Ellis et al., 1998; Ellis et al., 1999). In the fetus with dilated cardiomyopathy there was extensive staining for PCV-2 antigen throughout the affected myocardium. Staining was most extensive in areas of necrosis and appeared to involve primarily myocytes. Both cytoplasmic and nuclear staining was present. In multiple fetuses there was extensive staining in the liver. In some sections it appeared to involve primarily sinusoidal endothelium and Kupfer cells, while in other fetuses, including the one with myocarditis, there was also nuclear and cytoplasmic staining of hepatocytes. Positively stained cells were scattered throughout the lung, and multifocally in the kidney. Polymerase chain reaction for PCV-2 was performed as previously described using frozen tissue (Ellis et al., 1999). PCR product of the expected size for PCV-2 was amplified from fetal tissue. PCV-2 was isolated from the fetus with myocarditis and a pool of tissues from other fetuses in the litter by inoculating tissue homogenates onto PCV-free PK-15 cells.

Fetal tissues were also examined for other viral pathogens that have been associated with fetal injury and abortions in swine, including, porcine parvovirus (PPV), porcine reproductive and respiratory syndrome virus (PRRSV), encephalomyocarditis (EMCV), and enteroviruses. PPV antigen was not detected by fluorescent antibody testing (FAT) on frozen sections of lung, liver, and spleen from the mummified or stillborn fetuses. Homogenates of liver, lung, and spleen from the aborted fetuses were also inoculated into cultures of PCV-free PK-15 cells, primary porcine fallopian tube cells and Vero cells. Cytopathic viruses were not detected after three passages. Tissues were negative for PPV using PCR. PRRSV antigen was not detected by immunohistochemical staining.

Thus, there were fetal lesions and abortion directly associated with PCV-2. These results also show vertical transmission of the virus.

In a previous study, PCV-1 was isolated from 2 of 160 pig fetuses examined, implying that this group of viruses can be vertically transmitted; however, PCV-1 antigen could not be associated with any lesions in the tissue (Allan et al., 1995). The exclusion of other agents that have been associated with fetal lesions and abortion in swine, including, PPV (Bolt et al., 1997; Molitor et al., 1991), PRRSV (Lager et al., 1996), EMCV (Kim et al., 1989), and enterovirus (Molitor et al., 1991) indicate that PCV-2 can cause significant fetal pathology and subsequent abortion.

However, PCV-1 immunogens (still according to the general definition given at the beginning) may elicit an immunogenic or protective response against myocarditis and/or abortion and/or intrauterine infection as well as post-weaning multisystemic wasting syndrome and ergo PCV-1 immunogens can also be used in the practice of this invention (e.g., in the methods, compositions, uses, etc.)—either alone or in conjunction with PCV-2 immunogens (the vector can contain and express DNA encoding for both a PCV-1 immunogen and/or epitope and a PCV-2 immunogen and/or epitope) and/or alone or in conjunction an immunogen and/or epitope of other porcine pathogen (if a vector is used, the vector can contain and express DNA encoding for both a PCV-1 immunogen and/or epitope and an immunogen and/or epitope of another porcine pathogen, or for a PCV-1 immunogen and/or epitope and a PCV-2 immunogen and/or epitope and an immunogen and/or epitope of another porcine pathogen). Thus, one skilled in the art may alternatively or additionally use a PCV-1 immunogen, and/or epitope and/or vector encoding such an immunogen and/or epitope in the practice of this invention without any undue experimentation; for instance, to so do, one need only read the text herein prior to this Example and at the conclusion of (after) this Example, and substitute—PCV-1—for "PCV-2" with any modification minor based on teachings herein.

The wasting syndrome associated with PCV-2 infection most often occurs in 5–12 week old pigs (Allan et al., 1998; Ellis et al., 1998). Experimental infection of neonatal swine indicates a relatively long prodromal period between infection and the development of clinical signs associated with PCV-2 (Allan et al. 1999; Ellis et al. 1999). The findings herein show that the virus is transmitted vertically or in the perinatal period. Not only may interuterine vertical transmission of PCV-2 result in abortion, but it is possible that sublethally in utero-infected piglets may be the animals that subsequently develop PMWS.

Furthermore, these results show that inoculation of female pigs with a composition comprising an PCV-2 immunogen (which composition can also include an immunogen from another porcine pathogen, e.g., porcine parvovirus), prior to breeding or serving, or prior to the perinatal period and/or during gestation can prevent myocarditis and/or abortion and/or intrauterine infection associated with porcine circovirus-2, as well as post-weaning multisystemic wasting syndrome and other pathologic sequelae associated with PCV-2, by eliciting an immunological response or antibodies against PCV-2.

Of course, compositions, methods, and other aspects of the invention can be used or practiced in animals other than pigs, e.g., sheep, bison, cattle, wild boar; for instance, if PCV-2 infects such other animals.

Example/Result 2

Myocarditis, Abortion and Intrauterine Infection Associated with PCV-2

The presence of PCV-2 in neonatal piglets suggests that vertical transmission may be an important means of viral transmission. This mode of transmission may be related not only to reproductive failure, but also to the development of multisystemic disease later in life. It is of interest to determine whether previously undetected PCV-2 (and PCV-1) has been vertically transmitted in pork producing areas where PMWS, and by extension PCV-2 infection, has been endemic for at least several years.

Thirty eight submissions involving reproductive failure received in the diagnostic laboratory at the Western College of Veterinary Medicine (WCVM), University of Saskatchewan, Saskatoon, Canada, over a four-year period from a total of 30 high health herds in Canada were evaluated. Five of the farms from which the samples were obtained had diagnosed cases of PMWS. Twenty-seven of the thirty-eight submissions (71%) were classified as abortions; five of these (13%) also involved at least one mummified fetus. Of the remaining 10 cases: 5 involved stillborn piglets along, with nonviable piglets (13%); 2 with stillborn and one or more mummified feti (5%); 2 with only stillborn piglets (5%); and one with only mummified feti (2.5%). Routine diagnostics for pathogens other than circovirus revealed 4 cases (11%) in which the etiology was determined to be porcine parvovirus and 2 cases (5%) in which the etiology was determined to be of bacterial origin. Gross necropsies were performed and tissues were collected and fixed in buffered formalin (fixation time 24–72 hrs) and, in most cases, fresh tissues were also submitted for routine microbiological evaluation. None of these cases had been previously tested for PCV-2.

The PCR technique used for the detection of PCV-1 and PCV-2 was performed as previously described (Tischer et al. 1974). PCV-1 was not detected by PCR in any submissions comprising reproductive failure from the four-year period. PCV-2 was detected by PCR in two different submissions that originated from the same multi-site pork production unit on two separate occasions in the spring of the last year in the four-year period. The first of these submissions comprised a litter of piglets with gross evidence of myocarditis, cardiac hypertrophy, and chronic passive congestion.

Immunohistochemical identification of PCV-2 in tissues was performed as previously described (Tischer et al. 1974). Immunohistochemical staining (IHC) for PCV-2 was positive in hearts from all six of the piglets that were submitted, while 4 of 6 were positive by PCV-2 PCR (see following Table 3).

TABLE 3

Detection of PCV-2 in the formalin fixed hearts of porcine with myocarditis by PCR, IHC and viral isolation in cell culture

| PCV-2 positive tissues | PCR | IHC | Virus Isolation |
|---|---|---|---|
| Fixed | 5/6 | 6/6 | N/A |
| Frozen | 4/4 | N/A | 2/4 |

The second submission from the same farm consisted of a litter of four piglets in which 2 were stillborn and 2 others died shortly after birth. All four piglets also had gross evidence of a severe, difuse myocarditis, cardiac hypertrophy, and chronic passive congestion. Only fresh frozen heart, and pooled lung/spleen tissues were submitted for analysis. PCV-2 PCR was positive in the hearts of 2 of 4 piglets and in the pooled lung and splenic tissues of 4 of 4 piglets. Isolation of PCV-2 from affected hearts and/or pooled lung and splenic tissue was positive in 2 of the 4 cases that were PCV-2 positive by PCR. Based on serology and/or PCR, other agents associated with reproductive failure in swine, including porcine reproductive and respiratory syndrome virus and porcine parvovirus were apparently circulating in the breeding herd. However, these agents could not be shown to be associated with the severe cardiac (or other) lesions in the affected piglets; but, they may contribute to PMWS.

PCV-2 was not detected by PCR or IHC in any representative cases of reproductive failure submitted during the first three years of the four-year period (it was detected in cases of reproductive failure submitted during the last year of the four-year period). In order to rule out damage to DNA due to formalin fixation as a possible adverse factor limiting the ability to detect PCV-2 by PCR, PCR was performed on tissues collected from four weanling piglets with PMWS, PCV-2 DNA was amplified in all fixed tissues tested, including; lung, liver, kidney and bronchial lymph node, from all four individuals. Moreover, the sensitivity of the PCR PCV-2 was independent of the length of time that each tissue was fixed in formalin.

These results confirm and extend the previous observation (West et al. 1999) that PCV-2 can be vertically transmitted and can be present in large amounts within lesions from piglets infected in utero. Vertical transmission of PCV-2 virus and resultant fetal damage, such as myocarditis, is an additional disease manifestation of PCV-2. Furthermore, the failure to detect PCV-2 in cases of reproductive failure prior to the last year of the four-year period from an endemic area of PCV-2 infection may indicate that vertical transmission was not the primary mechanism responsible for the initial dissemination of viral infection. Sexual, as well as vertical, modes of transmission can be attributed to the spread of PCV-2 infection in pigs.

Example/Result 3

Culture and Isolation of the Porcine Circovirus Strains

Viruses 1103 and 1021 were isolated respectively in Alberta, respectively Saskatoon, Canada, from abortive cases according to the method described in J. Ellis et al. Can. J. Vet. 1998, vol 39, 44–51.

Viral culture is carried out on PK/15 cell cultures, known to be uncontaminated with the porcine circovirus (PCV), pestiviruses, porcine adenoviruses and porcine parvoviruses (Allan G. et al Pathogenesis of porcine circovirus experimental infections of colostrum-deprived piglets and examination of pig foetal material. Vet. Microbiol. 1995, 44, 49–64).

Monolayers of PK/15 cells are dissociated by trypsinization (with a trypsin-versene mixture) from confluent cultures, and taken up in MEM-SA medium containing 15% foetal calf serum not contaminated by pestivirus (=MEM-G medium) in a final concentration of about 400,000 cells per ml. 10 ml aliquot fractions of this cell suspension are then mixed with 2 ml aliquot fractions of the inocula described above, and the final mixtures is aliquoted in 6 ml volumes in two Falcon flasks of 25 cm$^2$. These cultures are then incubated at +37° C. for 18 hours under an atmosphere containing 10% $CO_2$.

After incubation, the culture medium of the semi-confluent monolayers were treated with 300 mM D-glucosamine (Cat # G48175, Sigma-Aldrich Company Limited, Poole, UK) (Tischr I. et al., Arch. Virol., 1987 96 39–57), then incubation was continued for an additional period of 48–72 hours at +37° C. Following this last incubation, one of the two Falcons of each inoculum was subjected to 3 successive freeze/thaw cycles. The PK/15 cells of the remaining Falcon were treated with a trypsin-versene solution, resuspended in 20 ml of MEM-G medium, and then inoculated into 75 cm$^2$ Falcons at a concentration of 400,000 cells/ml. The freshly inoculated flasks were then "superinfected" by addition of 5 ml of the corresponding lysate obtained after the freeze/thaw cycles.

Example/Result 4

Technique for the Detection of PCV by Immunofluorescence

The initial screening of all the cell culture preparations fixed with acetone was carried out by an indirect immunofluorescence technique (IIF) using a 1/100 dilution of a pool of adult pig sera. This pool of sera comprises sera from 25 adult sows from Northern Ireland and is known to contain antibodies against a wide variety of porcine viruses, including PCV: porcine parvovirus, porcine adenovirus, and PRRS virus. The IIF technique was carried out by bringing the serum (diluted in PBS) into contact with the cell cultures for one hour at +37° C., followed by two washes in PBS. The cell cultures were then stained with a 1/80 dilution in PBS of a rabbit anti-pig immunoglobulin antibody conjugated with fluorescein isothiocyanate for one hour, and then washed with PBS and mounted in glycerol buffer prior to the microscopic observation under ultraviolet light.

Example/Result 5

Production of PCV Antigens by In Vitro Culture

The culture of the noncontaminated PK/15 cells and the viral multiplication were carried out according to the same methods as in Example 1. The infected cells are harvested after trypsinization after 4 days of incubation at 37° C. and enumerated. The next passage is inoculated with 400,000 infected cells per ml.

The various PCV-2 strains disclosed herein, e.g. strains 1103 and 1121 are so cultivated.

Example/Result 6

Titration of PCV-2

Titration is carried out in 96-well microplates. A suspension of PK/15 cells (150 000 cells per ml) is first introduced (100 µl per well). Then dilutions of the viral culture are done and 100 µl thereof are introduced in the wells. Incubation is done at 37° C. with $CO_2$. After 24 h, there is carried out a treatment with glucosamine half an hour at 37° C. (for the conditions see example 3). The culture medium is then removed and fresh medium is introduced. Incubation is conducted 72 h at 37° C. Revelation of the foci is done using an anti-PCV-2 monoclonal antibody and a FITC labelled mouse conjugate.

This method can be used to titration for preparing inactivated as well as live attenuated PCV-2.

Example/Result 7

Inactivation of the Viral Antigens

At the end of the viral culture, the infected cells are harvested and lysed using ultrasound (Branson Sonifier) or with the aid of a rotor-stator type colloid mill (UltraTurrax, IKA). The suspension is then centrifuged at 3700 g for 30 minutes. The viral suspension is inactivated with 0.1% ethyleneimine for 18 hours at +37° C. or with 0.5% beta-propiolactone for 24 hours at +28° C. If the virus titre before inactivation is inadequate, the viral suspension is concentrated by ultrafiltration using a membrane with a 300 kDa cut-off (Millipore PTMK300). The inactivated viral suspension is stored at +5° C.

Example/Result 8

Preparation of the Vaccine in the Form of an Emulsion Based on Mineral Oil

The vaccine is prepared according to the following formula:

| | |
|---|---|
| suspension of inactivated porcine circovirus: | 250 ml |
| Montanide ® ISA 70 (SEPPIC): | 750 ml |

The aqueous phase and the oily phase are sterilized separately by filtration. The emulsion is prepared by mixing and homogenizing the ingredients with the aid of a Silverson turbine emulsifier.

One vaccine dose contains about $10^{7.5}$ TCID50. The volume of one vaccine dose is 0.5 ml for administration by the intradermal route, and 2 ml for administration by the intramuscular route.

This vaccine is used in a vaccination programme against the multisystemic wasting syndrome in combination with the Parvovax® vaccine.

Example/Result 9

Preparation of the Vaccine in the Form of a Metabolizable Oil-Based Emulsion The vaccine is prepared according to the following formula:

| | |
|---|---|
| suspension of inactivated porcine circovirus | 200 ml |
| Dehymuls HRE 7 (Henkel): | 60 ml |
| Radia 7204 (Oleofina): | 740 ml |

The aqueous phase and the oily phase are sterilized separately by filtration. The emulsion is prepared by mixing and homogenizing the ingredients with the aid of a Silverson turbine emulsifier.

One vaccine dose contains about $10^{7.5}$ TCID50. The volume of one vaccine dose is 2 ml for administration by the intramuscular route.

This vaccine is used in a vaccination programme against the multisystemic wasting syndrome in combination with the Parvovax® vaccine.

Example/Result 10

Vaccination of Piglets with DNA (Plasmid) Vector

Groups of 3 or 4 piglets, caesarian-derived day 0 are placed into isolators. The piglets are vaccinated day 2 either with (A) a plasmid comprising ORF 13 or with (B) a mixture of this plasmid and another plasmid comprising ORF 4, and with a physiological solution for the control group. Each plasmid is diluted in sterile physiological solution (NaCl 0.9%) at 250 µg/µl final concentration. A 2 ml volume is injected by intramuscular route in two points of 1 ml (1 point each side of the neck). A second injection of vaccine or placebo is administered day 14. Vaccination with DNA is well tolerated by piglets and no evidence for adverse reaction to vaccination is noted. The piglets are challenged day 21 by oronasal administration of PCV-2 viral suspension, 1 ml in each nostril. After challenge piglets are weighed once a week. Rectal temperatures are recorded on days 17, 21, 22, 24, 27, 29, 31, 34, 37, 41, 44. Day 44 fecal swabs are collected from each piglet for PCV-2 shedding. The virus is detected and quantified by quantitative PCR. Day 45 necropsies are performed and tissue samples are collected for virus isolation.

Clinical Symptoms:

There is no significant difference for the mean body weight gains or the mean body temperatures between groups.

Necropsy Lesions

The only gross finding noted in pigs at termination is bronchial lymphadenopathy. The lesions are scored according the following criteria.

0=no visible enlargement of lymph nodes

1=mild lymph nodes enlargement, restricted to bronchial lymph nodes

2=moderate lymph nodes enlargement, restricted to bronchial lymph nodes

3=severe lymph nodes enlargement, extended to bronchial submandibullar prescapsular and inguinal lymph nodes.

std is an abbreviation for standard deviation

| Groups | Lymphadenopathy scores | | |
|---|---|---|---|
| | mean | std | N |
| (A) | 1.2 | 1.3 | 4 |
| (B) | 2.0 | 1.7 | 3 |
| controls | 3.0 | 0.0 | 3 |

N = number of piglets in each group

A reduction of the lymph node lesions is observed in 3 out 4 piglets immunized with (A) and 1 out 3 piglets immunized with (B) mixture. This difference is not significant (p>0.05) due to the high value of the standard deviations (std).

Virus Load in Lymph Nodes Tissues:

Quantitative virus re-isolation is performed on tissue homogenates prepared from bronchial and mesenteric lymph nodes.

The data presented correspond to the virus titers in tissue homogenates after transformation in $\log_{10}$.

| | PCV-2 titers | | | | |
|---|---|---|---|---|---|
| | Bronchial LN | | Mesenteric LN | | |
| Groups | mean | std | mean | std | N |
| (A) | 0.9 | 0.8 | 0.9 | 0.8 | 4 |
| (B) | 0.7 | 0.6 | 0.2 | 0.2 | 3 |
| Controls | 2.0 | 1.1 | 1.8 | 1.1 | 4 |

Bronchial lymph nodes seem to contain the most infectious virus. A reduction of the viral load is observed in bronchial and mesenteric lymph nodes from piglets immunized with either (A) or (B) mixture. This reduction is significant (p # 0.05 for the plasmids mixture.

Viral Excretion:

Post challenge fecal swabs are assessed for schedding PCV-2 by PCR based on amplification of PCV-2 ORF 13. Each assay is performed in triplicate on 2 ml of sample. Unvaccinated controls are negative for PCV-2 prior challenge and positive after challenge confirming the validity of the PCR assay.

Values are expressed as $\log_{10}$ (number of molecules of PCV-2 DNA in 2 µl sample).

| | $\text{Log}_{10}$ number of PCV-2 DNA molecules | | |
|---|---|---|---|
| Groups | mean | std | N |
| (A) | 3.3 | 0.3 | 4 |
| (B) | 2.9 | 0.7 | 3 |
| Controls | 3.6 | 0.6 | 4 |

The differences between groups are not significant (p>0.05).

Example/Result 11

Vaccination of Piglets with Canarypox Live Vector and Results

Groups of 3 or 4 piglets, caesarian-derived day 0 are placed into isolators. Day 2 the piglets are vaccinated with $10^8$ pfu of (C) a canarypox comprising ORF 13, or (D) of a canarypox comprising ORF 13 and ORF 4, or parental canarypox, in 1 ml of PBS, by intramuscular route on the side of the neck. A second injection of vaccine or placebo is administered at day 14. Vaccination with canarypox is well tolerated by piglets and no evidence for adverse reaction to vaccination is noted The piglets are challenged day 21 by oronasal administration of a PCV-2 viral suspension, 1 ml in each nostril. Day 45 necropsies are performed and samples of tissues are collected for virus isolation.

Necropsy Results:

PMWS is characterized generally by lymphadenopathy and more rarely by hepatitis or nephritis. So the gross findings in lymph nodes are scored for each piglet in the following manner: 0=no visible enlargement of lymph nodes; 1=mild lymph nodes enlargement, restricted to bronchial lymph nodes; 2=moderate lymph nodes enlargement, restricted to bronchial lymph nodes; 3=severe lymph nodes enlargement, extended to bronchial, submandibullar prescapular and inguinal lymph nodes.

| Groups | Scores |
| --- | --- |
| (C) | 0.5 |
|  | 0.0 |
|  | 0.0 |
|  | 1.0 |
| mean | 0.38 |
| standard deviation | 0.48 |
| (D) | 0.0 |
|  | 0.5 |
|  | 0.5 |
|  | 1.0 |
| mean | 0.5 |
| standard deviation | 0.41 |
| Controls | 2.0 |
|  | 2.5 |
|  | 2.5 |
|  | 2.5 |
| mean | 2.38 |
| standard deviation | 0.25 |

Bronchial lymphadenopathy for PCV-2 is a prominent gross finding. A significant reduction of the lymph nodes lesion in relation to control group is observed after immunization with (C) and (D) ($p \leq 0.05$).

This invention is further described by the following statements:

1. An immunological, immunogenic or vaccine composition for the prevention and/or treatment of porcine circovirus-2 (PCV-2)-caused myocarditis, and/or abortion and/or intrauterine infection and/or post-weaning multisystemic wasting syndrome and/or other pathologic sequelae associated with PCV-2 comprising a pharmaceutically or veterinarily or medically acceptable carrier and an active agent comprising a PCV-2 immunogen, or a polypeptide comprising an epitope of a PCV-2 immunogen, or an antibody elicited by a PCV-2 immunogen, or an antibody elicited by an epitope of a PCV-2 immunogen, or a vector expressing a PCV-2 immunogen, or a vector expressing an epitope of a PCV-2 immunogen, or a PCV-1 immunogen that also binds to an antibody elicited by a PCV-2 immunogen or epitope, or a polypeptide comprising an epitope of a PCV-1 immunogen that also binds to an antibody elicited by a PCV-2 immunogen or epitope, or an antibody elicited by a PCV-1 immunogen that binds with both a PCV-1 immunogen or epitope and a PCV-2 epitope or immunogen, or an antibody elicited by an epitope of a PCV-1 immunogen that binds with both a PCV-1 immunogen or epitope and a PCV-2 epitope or immunogen, or a vector expressing a PCV-1 immunogen that also binds to an antibody elicited by a PCV-2 immunogen or epitope, or a vector expressing an epitope of a PCV-1 immunogen that also binds to an antibody elicited by a PCV-2 immunogen or epitope.

2. The composition of statement 1 for the prevention of PCV-2-caused mycarditis and/or abortion and/or intrauterine infection comprising a pharmaceutically or veterinarily or medically acceptable carrier and an active agent comprising a PCV-2 immunogen or a polypeptide comprising an epitope of a PCV-2 immunogen or an antibody elicited by a PCV-2 immunogen or an antibody elicited by an epitope of a PCV-2 immunogen or a vector expressing a PCV-2 immunogen or a vector expressing an epitope of a PCV-2 immunogen.

3. The composition of statement 2 wherein the composition comprises a PCV-2 immunogen.

4. The composition of statement 2 wherein the composition comprises a polypeptide comprising an epitope of a PCV-2 immunogen.

5. The composition of statement 2 wherein the composition comprises an antibody elicited by a PCV-2 immunogen.

6. The composition of statement 2 wherein the composition comprises an antibody elicited by an epitope of a PCV-2 immunogen.

7. The composition of statement 2 wherein the composition comprises a vector expressing a PCV-2 immunogen.

8. The composition of statement 2 wherein the composition comprises a vector expressing an epitope of a PCV-2 immunogen.

9. The composition of statement 3 wherein the PCV-2 immunogen is a porcine circovirus.

10. The composition of statement 9 wherein the PCV-2 immunogen comprises attenuated live whole PCV-2.

11. The composition of statement 9 wherein the PCV-2 immunogen comprises inactivated PCV-2.

12. The composition of statement 3 wherein the composition is a subunit immunogenic, immunological or vaccine composition.

13. The composition of any one of statements 3, 4, 5, 6, 9, 10, 11, or 12 additionally including at least one immunogen or epitope from at least one additional pig pathogen or a vector expressing such an immunogen or epitope.

14. The composition of statement 13 wherein the composition additionally includes at least one antig immunogen en or epitope from at least one additional pig pathogen.

15. The composition of statement 13 wherein the at least one additional pig pathogen is selected from the group consisting of PRRS, *Mycoplasma hyopneumoniae, Actinobacillus pleuropneumoniae, E. coli,* Atrophic Rhinitis, Pseudorabies, Hog cholera, Swine Influenza, encepaphalomyocarditis virus, and PPV.

16. The composition of statement 13 wherein the at least one additional pig pathogen comprises PPV.

17. The composition of statement 7 or 8 wherein the vector comprises a DNA vector plasmid, a *E. coli*, a baculovirus, a pig herpes viruses, including Aujeszky's disease virus, a porcine adenovirus, a poxvirus, including a vaccinia virus, an avipox virus, a canarypox virus, and a swinepox virus.

18. The composition of statement 17 wherein the vector comprises a DNA vector.

19. The composition of statement 17 wherein the vector comprises a canarypox virus.

20. The composition of statement 7 or 8 additionally including at least one immunogen or epitope from at least one additional pig pathogen, or a vector expressing such an immunogen or epitope, wherein the vector can also be the vector expressing the PCV-2 immunogen or epitope.

21. The composition of statement 17 additionally including at least one immunogen or epitope from at least one additional pig pathogen, or a vector expressing such an immunogen or epitope, wherein the vector can also be the vector expressing the PCV-2 immunogen n or epitope.

22. The composition of statement 20 wherein the at least one additional pig pathogen is selected from the group consisting of PRRS, *Mycoplasma hyopneumoniae, Actinobacillus pleuropneumoniae, E. coli,* Atrophic Rhinitis, Pseudorabies, Hog cholera, Swine Influenza, encepaphalomyocarditis virus, and PPV.

23. The composition of statement 21 wherein the at least one additional pig pathogen is selected from the group consisting of PRRS, *Mycoplasma hyopneumoniae, Actino-*

*bacillus pleuropneumoniae, E. coli*, Atrophic Rhinitis, Pseudorabies, Hog cholera, Swine Influenza, encepaphalomyocarditis virus, and PPV.

24. The composition of statement 7 wherein the vector contains and expresses an ORF selected from the group consisting of ORFs 1 to 13.

25. The composition of statement 17 wherein the vector contains and expresses an ORF selected from the group consisting of ORFs 1 to 13.

26. The composition of statement 24 wherein the vector contains and expresses an ORF selected from ORFs 4, 7, 10 and 13

27. The composition of statement 25 wherein the vector contains and expresses an ORF selected from ORFs 4, 7, 10 and 13

28. The composition of statement 24 wherein the vector contains and expresses ORF 4 and/or 13

29. The composition of statement 24 wherein the vector contains and expresses ORF 4 and/or 13

30. The composition of statement 3 or 4 wherein the immunogen or epitope is recombinantly produced.

31. A method for the prevention and/or treatment of porcine circovirus-2 (PCV-2)-caused myocarditis, and/or abortion and/or intrauterine infection and/or post-weaning multisystemic wasting syndrome and/or other pathologic sequelae associated with PCV-2 comprising a inducing an immunological, immunogenic or protective response against PCV-2 in a pig comprising administering to the pig a composition comprising a pharmaceutically or veterinarily or medically acceptable carrier and an active agent comprising a PCV-2 immunogen, or a polypeptide comprising an epitope of a PCV-2 immunogen, or an antibody elicited by a PCV-2 immunogen, or an antibody elicited by an epitope of a PCV-2 immunogen, or a vector expressing a PCV-2 immunogen, or a vector expressing an epitope of a PCV-2 immunogen, or a PCV-1 immunogen that also binds to an antibody elicited by a PCV-2 immunogen or epitope, or a polypeptide comprising an epitope of a PCV-1 immunogen that also binds to an antibody elicited by a PCV-2 immunogen or epitope, or an antibody elicited by a PCV-1 immunogen that binds with both a PCV-1 immunogen or epitope and a PCV-2 epitope or immunogen, or an antibody elicited by an epitope of a PCV-1 immunogen that binds with both a PCV-1 immunogen or epitope and a PCV-2 epitope or immunogen, or a vector expressing a PCV-1 immunogen that also binds to an antibody elicited by a PCV-2 immunogen or epitope, or a vector expressing an epitope of a PCV-1 immunogen that also binds to an antibody elicited by a PCV-2 immunogen or epitope.

32. The method of statement 31 for the prevention of PCV-2-caused mycarditis and/or abortion and/or intrauterine infection comprising administering a composition comprising a pharmaceutically or veterinarily or medically acceptable carrier and an active agent comprising a PCV-2 immunogen or a polypeptide comprising an epitope of a PCV-2 immunogen or an antibody elicited by a PCV-2 immunogen or an antibody elicited by an epitope of a PCV-2 immunogen or a vector expressing a PCV-2 immunogen or a vector expressing an epitope of a PCV-2 immunogen.

33. The method of statement 32 wherein the composition comprises a PCV-2 immunogen.

34. The method of statement 32 wherein the composition comprises a polypeptide comprising an epitope of a PCV-2 immunogen.

35. The method of statement 32 wherein the composition comprises an antibody elicited by a PCV-2 immunogen.

36. The method of statement 32 wherein the composition comprises an antibody elicited by an epitope of a PCV-2 immunogen.

37. The method of statement 32 wherein the composition comprises a vector expressing a PCV-2 immunogen.

38. The method of statement 32 wherein the composition comprises a vector expressing an epitope of a PCV-2 immunogen.

39. The method of statement 33 wherein the PCV-2 immunogen is a porcine circovirus.

40. The method of statement 39 wherein the PCV-2 immunogen comprises attenuated live whole PCV-2.

41. The method of statement 39 wherein the PCV-2 immunogen comprises inactivated PCV-2.

42. The method of statement 33 wherein the composition is a subunit immunogenic, immunological or vaccine composition.

43. The method of any one of statements 33, 34, 35, 36, 39, 40, 41, or 42 wherein the composition additionally includes at least one immunogen or epitope from at least one additional pig pathogen or a vector expressing such an immunogen or epitope.

44. The method of statement 43 wherein the composition additionally includes at least one immunogen or epitope from at least one additional pig pathogen.

45. The method of statement 43 wherein the at least one additional pig pathogen is selected from the group consisting of PRRS, *Mycoplasma hyopneumoniae, Actinobacillus pleuropneumoniae, E. coli*, Atrophic Rhinitis, Pseudorabies, Hog cholera, Swine Influenza, encepaphalomyocarditis virus, and PPV.

46. The method of statement 43 wherein the at least one additional pig pathogen comprises PPV.

47. The method of statements 37 or 38 wherein the vector comprises a DNA vector plasmid, a *E. coli*, a baculovirus, a pig herpes viruses, including Aujeszky's disease virus, a porcine adenovirus, a poxvirus, including a vaccinia virus, an avipox virus, a canarypox virus, and a swinepox virus.

48. The method of statement 47 wherein the vector comprises a DNA vector.

49. The method of statement 47 wherein the vector comprises a canarypox virus.

50. The method of statement 37 or 38 additionally including at least one immunogen or epitope from at least one additional pig pathogen, or a vector expressing such an immunogen or epitope, wherein the vector can also be the vector expressing the PCV-2 immunogen or epitope.

51. The method of statement 47 additionally including at least one immunogen or epitope from at least one additional pig pathogen, or a vector expressing such an immunogen or epitope, wherein the vector can also be the vector expressing the PCV-2 immunogen or epitope.

52. The method of statement 50 wherein the at least one additional pig pathogen is selected from the group consisting of PRRS, *Mycoplasma hyopneumoniae, Actinobacillus pleuropneumoniae, E. coli*, Atrophic Rhinitis, Pseudorabies, Hog cholera, Swine Influenza, encepaphalomyocarditis virus, and PPV.

53. The method of statement 51 wherein the at least one additional pig pathogen is selected from the group consisting of PRRS, *Mycoplasma hyopneumoniae, Actinobacillus pleuropneumoniae, E. coli*, Atrophic Rhinitis, Pseudorabies, Hog cholera, Swine Influenza, and PPV.

54. The method of statement 37 wherein the vector contains and expresses an ORF selected from the group consisting of ORFs 1 to 13.

55. The composition of statement 47 wherein the vector contains and expresses an ORF selected from the group consisting of ORFs 1 to 13.

56. The method of statement 54 wherein the vector contains and expresses an ORF selected from ORFs 4, 7, 10 and 13

57. The method of statement 55 wherein the vector contains and expresses an ORF selected from ORFs 4, 7, 10 and 13

58. The method of statement 54 wherein the vector contains and expresses ORF 4 and/or 13

59. The method of statement 55 wherein the vector contains and expresses ORF 4 and/or 13

60. The method of statements 33 or 34 wherein the immunogen or epitope is recombinantly produced.

61. The method of statement 32 wherein the pig is a female pig.

62. The method of statement 61 wherein the administering is prior to breeding.

63. The method of statement 61 wherein the administering is during pregnancy.

64. The method of statement 32 wherein the pig is a male pig.

65. A method for preparing the composition of statement 1 comprising admixing the pharmaceutically or veterinarily or medically acceptable carrier and the active agent comprising a PCV-2 immunogen, or a polypeptide comprising an epitope of a PCV-2 immunogen, or an antibody elicited by a PCV-2 immunogen, or an antibody elicited by an epitope of a PCV-2 immunogen, or a vector expressing a PCV-2 immunogen, or a vector expressing an epitope of a PCV-2 immunogen, or a PCV-1 immunogen that also binds to an antibody elicited by a PCV-2 immunogen or epitope, or a polypeptide comprising an epitope of a PCV-1 immunogen that also binds to an antibody elicited by a PCV-2 immunogen or epitope, or an antibody elicited by a PCV-1 immunogen that binds with both a PCV-1 immunogen or epitope and a PCV-2 epitope or immunogen, or an antibody elicited by an epitope of a PCV-1 immunogen that binds with both a PCV-1 immunogen or epitope and a PCV-2 epitope or immunogen, or a vector expressing a PCV-1 immunogen that also binds to an antibody elicited by a PCV-2 ant immunogen igen or epitope, or a vector expressing an epitope of a PCV-1 immunogen that also binds to an antibody elicited by a PCV-2 immunogen or epitope.

66. A kit for preparing the composition of statement 1 or for performing the method of statement 31 comprising in a first container the pharmaceutically or veterinarily or medically acceptable carrier and in a second container the active agent comprising a PCV-2 immunogen, or a polypeptide comprising an epitope of a PCV-2 immunogen, or an antibody elicited by a PCV-2 immunogen, or an antibody elicited by an epitope of a PCV-2 immunogen, or a vector expressing a PCV-2 immunogen, or a vector expressing an epitope of a PCV-2 immunogen, or a PCV-1 immunogen that also binds to an antibody elicited by a PCV-2 immunogen or epitope, or a polypeptide comprising an epitope of a PCV-1 immunogen that binds to an antibody elicited by a PCV-2 immunogen or epitope, or an antibody elicited by a PCV-1 immunogen that binds with both a PCV-1 immunogen or epitope and a PCV-2 epitope or immunogen, or an antibody elicited by an epitope of a PCV-1 immunogen that binds with both a PCV-1 immunogen or epitope and a PCV-2 epitope or immunogen, or a vector expressing a PCV-1 immunogen that also binds to an antibody elicited by a PCV-2 immunogen or epitoep, or a vector expressing an epitope of a PCV-1 immunogen that also binds to an antibody elicited by a PCV-2 immunogen or epitope; wherein the first and second containers are optionally packaged together, and the kit optionally includes instructions for admixture of ingredients of the composition and/or administration of the composition.

67. An isolated nucleic acid molecule comprising a sequence of the genome of 1103 strain or 1121 strain or a fragment thereof comprising an open reading frame or encoding an epitope or immunogen.

68. A vector comprising the isolated nucleic acid molecule of statement 67.

69. A PCV-2 immunogen or epitope from expression of the nucleic acid molecule of statement 67 or the vector of statement 68.

70. An immunological composition comprising the DNA molecule of statement 67 or the vector of statement 68.

71. An immunological composition comprising the immunogen or epitope of statement 69.

72. A method for inducing an immunological response comprising administering the vector of statement 68 or the nucleic acid molecule of statement 67, wherein there is in vivo expression of the nucleic acid molecule.

73. A method for inducing an immunological response comprising administering the immunological composition of statement 70, wherein there is in vivo expression of the nucleic acid molecule.

74. A method for inducing an immunological response comprising administering the immunogen or epitope of statement 69.

75. A method for inducing an immunological response comprising administering the immunological composition of statement 71.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications are variations of the method and apparatuses described herein will be obvious to those skilled in the art, and are intended to be encompassed by the following claims.

REFERENCES

1. Allan G M, McNeilly F, Cassady J P, et al.: 1995, Pathogenesis of porcine circovirus; experimental infections of colostrum deprived piglets and examination of pig foetal material. Vet Microbiol 44:49–641.

2. Allan G M, McNeilly F, Kennedy S, et al.: 1998, Isolation of porcine circovirus-like viruses from piglets with a wasting disease in the United States of America and Europe. J Vet Diag Invest 10:3–10.

3. Allan G M, Kennedy S, McNeilly F, et al.: 1999, Experimental reproduction of wasting disease and death by co-infection of pigs with porcine circovirus and porcine parvovirus, J Comp Path 121: 1–11 (July 1999).

4. Bolt D M, Hani H, Muller E, and Waldvogel A S: 1997, Nonsuppurative myocarditis in piglets associated with porcine parvovirus infection. J Comp Path 117:107–118.

5. Ellis, J A, Hassard L, Clark E G, et al.: 1998, Isolation of circovirus from lesions of piglets with postweaning multisystemic wasting syndrome. Can Vet J 39:44–51

6. Ellis J A, Krakowka S, Lairmore M, et al.: 1999, Reproduction of lesions of postweaning multisystemic wasting syndrome in gnotobiotic piglets. J Vet Diag Invest 11:3–14.

7. Kim H S, Jo H S and Bergeland M E: 1989, Serologic, virologic, and histopathologic observations of encephalomyocarditis virus infection in mummified and stillborn pigs. J Vet Diag Invest 1:101–104.

8. Lager K M and Halbur P G: 1996, Gross and microscopic lesions in porcine fetuses infected with porcine reproductive and respiratory syndrome virus. J Vet Diag Invest 8:275–282.

9. Meehan B M, McNeilly F. Todd D, et al.: 1998, Characterization of novel circovirus DNA's associated wasting disease syndromes in pigs. J Gen Virol 79:2171–2179.

10. Mengeling W L 1992, Porcine parvovirus. In: Diseases of swine, ed. Leman A D, 7th ed-, pp.299–311. Iowa State University Press, Ames, Iowa.

11. Molitor T W, Orveerakul K, Zhang Z Z, et al.: 1991, Polymerase chain reaction (PRC) amplification for detection of porcine parvovirus. J Virol Meth 32:201–211

12. Pensaert M and DeMeurichy W: 1973, A porcine enterovirus causing fetal death and mummification. Experimental infection of pregnant female pigs. Zentralbl Veterinaermed Beih 11:2025.

13. Tischer 1, Rasch R and Tochtermann G: 1974, Characterization of papovavirus- and picomavirus-like particles—in permanent piglet kidney cell lines. Zentralbl-Bakertiol-Org-A 226:153–167.

14. West K H, Bystrom, J M, Wojnarowicz C, et al.: 1999, Myocarditis and abortion associated with intrauterine infection of sows with porcine circovirus-2. J Vet Diag Invest 1.

We claim:

1. A method for reducing viral load of porcine circovirus-2 (PCV-2) in a pig comprising inducing an immunological or immunogenic response against PCV-2 in the pig comprising administering to the pig a composition comprising a pharmaceutically or veterinarily or medically acceptable carrier and an active agent comprising a vector containing an exogenous nucleotide sequence, wherein the nucleotide sequence encodes and expresses PCV-2 ORF4, PCV-2 ORF13 or PCV-2 ORF4 and ORF13.

2. A method for reducing viral load of porcine circovirus-2 (PCV-2) in a pig comprising inducing an immunological or immunogenic response against PCV-2 in the pig comprising administering to the pig a composition comprising a pharmaceutically or veterinarily or medically acceptable carrier and an active agent comprising a vector containing an exogenous nucleotide sequence, wherein the nucleotide sequence encodes and expresses PCV-2 ORF13.

3. The method of claim 1 or claim 2, wherein the composition additionally comprises at least one immunogen from at least one additional pig pathogen or a vector expressing such an immunogen.

4. The method of claim 3 wherein the composition additionally includes at least one immunogen from at least one additional pig pathogen.

5. The method of claim 3 wherein the at least one additional pig pathogen is selected from the group consisting of PRRS, *Mycoplasma hyopneumoniae, Actinobacillus pleuropneumoniae, Escherichia coli*, atrophic rhinitis, pseudorabies, hog cholera, swine influenza, encephalomyocarditis virus, and PPV.

6. The method of claim 5, wherein the at least one additional pig pathogen is PPV.

7. The method of claim 1 or claim 2, wherein the vector comprises a DNA plasmid, an *E. coli* cell, a baculovirus, a pig herpes virus, Aujeszky's disease virus, a porcine adenovirus, or a poxvirus.

8. The method of claim 7, wherein the vector is a DNA plasmid.

9. The method of claim 7, wherein the vector is a canarypox virus.

10. The method of claim 1, additionally comprising at least one immunogen from at least one additional pig pathogen, or a vector expressing such an immunogen, wherein the vector expressing the immunogen can also be the vector expressing PCV-2 ORF4, or PCV-2 ORF13 or PCV-2 ORF 4 and ORF13.

11. The method of claim 10 wherein the at least one additional pig pathogen is selected from the group consisting of PRRS, *Mycoplasma hyopneumoniae, Actinobacillus pleuropneumoniae, Escherichia coli*, atrophic rhinitis, pseudorabies, hog cholera, swine influenza, encepaphalomyocarditis virus, and PPV.

12. The method of claim 1 or claim 2, wherein the administering is prior to breeding.

13. The method of claim 1 or claim 2, wherein the pig is a pregnant female pig.

14. The method of claim 1, wherein the vector contains and expresses PCV-2 ORF4 and ORF13.

15. The method of claim 1, wherein the vector contains and expresses PCV-2 ORF4.

*

SEQUENCE LISTING

<160> NUMBER OF SEQ ID NOS: 8

<210> SEQ ID NO 1
<211> LENGTH: 1767
<212> TYPE: DNA
<213> ORGANISM: Porcine circovirus

<400> SEQUENCE: 1

```
aattcaacct taacctttct tattctgtag tattcaaagg gcacagagcg ggggtttgag      60
cccctcctg ggggaagaaa gtcattaata ttgaatctca tcatgtccac cgcccaggag     120
ggcgttctga ctgtggttcg cttgacagta tatccgaagg tgcgggagag gcgggtgttg    180
aagatgccat ttttccttct ccagcggtaa cggtggcggg ggtggacgag ccaggggcgg    240
cggcggagga tctggccaag atggctgcgg gggcggtgtc ttcttctccg gtaacgcctc    300
cttggatacg tcatatctga aaacgaaaga agtgcgctgt aagtattacc agcgcacttc    360
ggcagcggca gcacctcggc agcacctcag cagcaacatg ccgagcaaga agaatggaag    420
aagcggaccc caaccccata aaggtgggt gttcactctg aataatcctt ccgaagacga     480
gcgcaagaaa atacgggatc ttccaatatc cctatttgat tattttattg ttggcgagga    540
gggtaatgag gaaggacgaa cacctcacct ccaggggttc gctaattttg tgaagaagca    600
gacttttaat aaagtgaagt ggtatttggg tgcccgctgc cacatcgaga aagcgaaagg    660
aacagatcag cagaataaag aatactgcag taaagaaggc aacttactga tggagtgtgg    720
agctcctaga tctcagggac aacggagtga cctgtctact gctgtgagta ccttgttgga    780
gagcgggagt ctggtgaccg ttgcagagca gcaccctgta acgtttgtca gaaatttccg    840
cgggctggct gaactttga aagtgagcgg gaaaatgcag aagcgtgatt ggaagactaa     900
tgtacacgtc attgtgggc cacctgggtg tggtaaaagc aaatgggctg ctaatttgc      960
agacccggaa accacatact ggaaaccacc tagaaacaag tggtgggatg gttaccatgg   1020
tgaagaagtg gttgttattg atgacttta tggctggctg ccctgggatg atctactgag   1080
actgtgtgat cgatatccat tgactgtaga gactaaaggt ggaactgtac ctttttggc    1140
ccgcagtatt ctgattacca gcaatcagac cccgttggaa tggtactcct caactgctgt   1200
cccagctgta gaagctcttt atcggaggat tacttccttg gtatttttgga agaatgctac   1260
agaacaatcc acggaggaag ggggccagtt cgtcacccctt tccccccat gccctgaatt    1320
tccatatgaa ataaattact gagtcttttt tatcacttcg taatggtttt tattattcat   1380
taagggttaa gtgggggtc tttaagatta aattctctga attgtacata catggttaca   1440
```

-continued

```
cggatattgt attcctggtc gtatatactg ttttcgaacg cagtgccgag gcctacgtgg    1500
tctacatttc cagcagtttg tagtctcagc cacagctggt ttcttttgtt gtttggttgg    1560
aagtaatcaa tagtggaatc taggacaggt ttgggggtaa agtagcggga gtggtaggag    1620
aagggctggg ttatggtatg gcgggaggag tagtttacat aggggtcata ggtgagggct    1680
gtggcctttg ttacaaagtt atcatctaga ataacagcac tggagcccac tcccctgtca    1740
ccctgggtga tcggggagca gggccag                                        1767

<210> SEQ ID NO 2
<211> LENGTH: 1767
<212> TYPE: DNA
<213> ORGANISM: Porcine circovirus

<400> SEQUENCE: 2
aattcaacct taacctttct tattctgtag tattcaaagg gcacagagcg ggggtttgag      60
ccccctcctg ggggaagaaa gtcattaata ttgaatctca tcatgtccac cgcccaggag    120
ggcgttttga ctgtggttcg cttgacagta tatccgaagg tgcgggagag gcgggtgttg    180
aagatgccat ttttccttct ccagcggtaa cggtggcggg ggtggacgag ccaggggcgg    240
cggcggagga tctggccaag atggctgcgg ggcggtgtc ttcttctccg gtaacgcctc      300
cttggatacg tcatatctga aaacgaaaga agtgcgctgt aagtattacc agcgcacttc    360
ggcagcggca gcacctcggc agcacctcag cagcaacatg cccagcaaga gaatggaag      420 aagcggaccc caaccccata aaaggtgggt gttcactctg aataatcctt ccgaagacga    480
gcgcaagaaa atacgggatc ttccaatatc cctatttgat tattttattg ttggcgagga    540
gggtaatgag gaaggacgaa cacctcacct ccagggggttc gctaattttg tgaagaagca    600
gacttttaat aaagtgaagt ggtatttggg tgcccgctgc cacatcgaga agcgaaagg     660 aacagatcag cagaataaag aatactgcag taaagaaggc aacttactga tggagtgtgg    720
agctcctaga tctcagggac aacggagtga cctgtctact gctgtgagta ccttgttgga    780
gagcgggagt ctggtgaccg ttgcagagca gcaccctgta acgtttgtca gaaatttccg    840
cgggctggct gaacttttga agtgagcgg gaaaatgcag aagcgtgatt ggaagactaa     900 tgtcacgtc attgtggggc cacctggtgt tggtaaaagc aaatgggctg ctaattttgc    960
agacccggaa accacatact ggaaaccacc tagaaacaag tggtgggatg gttaccatgg    1020
tgaagaagtg gttgttattg atgactttta tggctggctg ccctgggatg atctactgag    1080
actgtgtgat cgatatccat tgactgtaga gactaaaggt ggaactgtac cttttttggc    1140
ccgcagtatt ctgattacca gcaatcagac cccgttggaa tggtactcct caactgctgt    1200
cccagctgta gaagctcttt atcggaggat tacttccttg gtattttgga gaatgctac     1260 agaacaatcc acggaggaag gggccagtt cgtcacccttt ccccccat gccctgaatt    1320 tccatatgaa ataaattact gagtctttttt tatcacttcg taatggtttt tattattcat    1380
taagggttaa gtgggggtc tttaagatta aattctctga attgtacata catggttaca    1440
cggatattgt attcctggtc gtatatactg ttttcgaacg cagtgccgag gcctacgtgg    1500
tctacatttc cagtagtttg tagtctcagc cacagctgat ttcttttgtt gtttggttgg    1560
aagtaatcaa tagtggaatc taggacaggt ttgggggtaa agtagcggga gtggtaggag    1620
aagggctggg ttatggtatg gcgggaggag tagtttacat aggggtcata ggtgagggct    1680
gtggcctttg ttacaaagtt atcatctaga ataacagcac tggagcccac tcccctgtca    1740
```

```
                                        -continued
ccctgggtga tcggggagca gggccag                                       1767

<210> SEQ ID NO 3
<211> LENGTH: 1768
<212> TYPE: DNA
<213> ORGANISM: Porcine circovirus

<400> SEQUENCE: 3
aattcaacct taaccttttt tattctgtag tattcaaagg gtatagagat tttgttggtc     60
cccccctccg gggaacaaa gtcgtcaata ttaaatctca tcatgtccac cgcccaggag    120
ggcgttctga ctgtggtagc cttgacagta tatccgaagg tgcgggagag gcgggtgttg    180
aagatgccat ttttccttct ccaacggtag cggtggcggg ggtggacgag ccaggggcgg    240
cggcggagga tctggccaag atggctgcgg ggcggtgtc ttcttctgcg gtaacgcctc    300
cttggatacg tcatagctga aaacgaaaga agtgcgctgt aagtattacc agcgcacttc    360
ggcagcggca gcacctcggc agcacctcag cagcaacatg cccagcaaga gaatggaag    420 aagcggaccc caaccacata aaggtgggt gttcacgctg aataatcctt ccgaagacga    480
gcgcaagaaa atacgggagc tcccaatctc cctatttgat tattttattg ttggcgagga    540
gggtaatgag gaaggacgaa cacctcacct ccagggggttc gctaattttg tgaagaagca    600
aacttttaat aaagtgaagt ggtatttggg tgcccgctgc cacatcgaga aagccaaagg    660
aactgatcag cagaataaag aatattgcag taaagaaggc aacttactta ttgaatgtgg    720
agctcctcga tctcaaggac aacggagtga cctgtctact gctgtgagta ccttgttgga    780
gagcgggagt ctggtgaccg ttgcagagca gcaccctgta acgtttgtca gaaatttccg    840
cgggctggct gaacttttga aagtgagcgg gaaaatgcag aagcgtgatt ggaagaccaa    900
tgtacacgtc attgtggggc cacctgggtg tggtaaaagc aaatgggctg ctaattttgc    960
agacccggaa accacatact ggaaaccacc tagaaacaag tggtgggatg gttaccatgg   1020
tgaagaagtg gttgttattg atgacttta tggctggctg ccgtgggatg atctactgag   1080
actgtgtgat cgatatccat tgactgtaga gactaaaggt ggaactgtac ctttttttggc   1140 ccgcagtatt ctgattacca gcaatcagac cccgttggaa tggtactcct caactgctgt   1200
cccagctgta gaagctctct atcggaggat tacttccttg gtattttgga agaatgctac   1260
agaacaatcc acggaggaag ggggccagtt cgtcacccctt tccccccat gccctgaatt   1320 tccatatgaa ataaattact gagtcttttt tatcacttcg taatggtttt tattattcat   1380 ttaggggttta agtggggggt ctttaagatt aaattctctg aattgtacat acatggttac   1440
acggatattg tagtcctggt cgtatatact gttttcgaac gcagtgccga ggcctacgtg   1500
gtccacattt ctagaggttt gtagcctcag ccaaagctga ttcctttttgt tatttggttg   1560 gaagtaatca atagtggagt caagaacagg tttgggtgtg aagtaacggg agtggtagga   1620 gaaggggttgg gggattgtat ggcgggagga gtagtttaca tatgggtcat aggttagggc   1680
tgtggccttt gttacaaagt tatcatctag aataacagca gtggagccca ctcccctatc   1740
accctgggtg atggggagc agggccag                                       1768

<210> SEQ ID NO 4
<211> LENGTH: 1768
<212> TYPE: DNA
<213> ORGANISM: Porcine circovirus

<400> SEQUENCE: 4
aattcaacct taaccttttct tattctgtag tattcaaagg gtatagagat tttgttggtc     60
```

-continued

```
cccctcccg ggggaacaaa gtcgtcaatt ttaaatctca tcatgtccac cgcccaggag      120
ggcgttgtga ctgtggtacg cttgacagta tatccgaagg tgcgggagag cgggtgttg      180 aagatgccat ttttccttct ccaacggtag cgtggcggg ggtggacgag ccaggggcgg      240
cggcggagga tctggccaag atggctgcgg gggcggtgtc ttcttctgcg gtaacgcctc      300
cttggatacg tcatagctga aaacgaaaga agtgcgctgt aagtattacc agcgcacttc      360
ggcagcggca gcacctcggc agcacctcag cagcaacatg cccagcaaga gaatggaag      420 aagcggaccc caaccacata aaggtgggt gttcacgctg aataatcctt ccgaagacga      480
gcgcaagaaa atacgggagc tcccaatctc cctatttgat tattttattg ttggcgagga      540
gggtaatgag gaaggacgaa cacctcacct ccaggggttc gctaattttg tgaagaagca      600 aactttaat aaagtgaagt ggtatttggg tgcccgctgc cacatcgaga aagccaaagg      660
aactgatcag cagaataaag aatattgcag taaagaaggc aacttactta ttgaatgtgg      720
agctcctcga tctcaaggac aacggagtga cctgtctact gctgtgagta ccttgttgga      780
gagcgggagt ctggtgaccg ttgcagagca gcaccctgta acgtttgtca gaaatttccg      840
cgggctggct gaacttttga agtgagcgg gaaaatgcag aagcgtgatt ggaagaccaa      900
tgtacacgtc attgtgggc cacctgggtg tggtaaaagc aaatgggctg ctaattttgc      960
agacccggaa accacatact ggaaaccacc tagaaacaag tggtgggatg gttaccatgg     1020
tgaagaagtg gttgttattg atgacttta tggctggctg ccgtgggatg atctactgag     1080
actgtgtgat cgatatccat tgactgtaga gactaaaggt ggaactgtac ctttttggc     1140 ccgcagtatt ctgattacca gcaatcagac cccgttggaa tggtactcct caactgctgt     1200
cccagctgta gaagctctct atcgaggat tacttccttg gtattttgga agaatgctac     1260
agaacaatcc acggaggaag ggggccagtt cgtcacccct tccccccat gccctgaatt     1320 tccatatgaa ataaaattact gagtcttttt tatcacttcg taatggttttt tattattcat     1380 ttagggttta agtgggggggt ctttaagatt aaattctctg aattgtacat acatggttac     1440
acggatattg tagtcctggt cgtatttact gttttcgaac gcagcgccga ggcctacgtg     1500
gtccacattt ccagaggttt gtagtctcag ccaaagctga ttcctttgt tatttggttg     1560 gaagtaatca atagtggagt caagaacagg tttgggtgtg aagtaacggg agtggtagga     1620
gaagggttgg gggattgtat ggcgggagga gtagtttaca tatgggtcat aggttagggc     1680
tgtggccttt gttacaaagt tatcatctag aataacagca gtggagccca ctcccctatc     1740
accctgggtg atggggagc agggccag                                         1768
```

<210> SEQ ID NO 5
<211> LENGTH: 1759
<212> TYPE: DNA
<213> ORGANISM: Porcine circovirus

<400> SEQUENCE: 5

```
aattcatatt tagcctttct aatacggtag tattggaaag gtaggggtag ggggttggtg       60
ccgcctgagg gggggaggaa ctggccgatg ttgaatttga ggtagttaac attccaagat      120
ggctgcgagt atcctccttt tatggtgagt acaaattctg tagaaaggcg ggaattgaag      180
atacccgtct ttcggcgcca tctgtaacgg tttctgaagg cggggtgtgc caaatatggt      240
cttctccgga ggatgtttcc aagatggctg cggggcggg tccttcttct gcggtaacgc      300
ctccttggcc acgtcatcct ataaaagtga agaagtgcg ctgctgtagt attaccagcg      360
```

```
cacttcggca gcggcagcac ctcggcagcg tcagtgaaaa tgccaagcaa gaaaagcggc    420
ccgcaacccc ataagaggtg ggtgttcacc cttaataatc cttccgagga ggagaaaaac    480
aaaatacggg agcttccaat ctccctttt gattattttg tttgcggaga ggaaggtttg    540
gaagagggta gaactcctca cctccagggg tttgcgaatt tgctaagaa gcagacttt    600 aacaaggtga agtggtattt tggtgcccgc tgccacatcg agaaagcgaa aggaaccgac    660
cagcagaata agaatactg cagtaaagaa ggccacatac ttatcgagtg tggagctccg    720
cggaaccagg ggaagcgcag cgacctgtct actgctgtga gtacccttt ggagacgggg    780 tctttggtga ctgtagccga gcagttccct gtaacgtatg tgagaaattt ccgcgggctg    840
gctgaacttt tgaaagtgag cgggaagatg cagcagcgtg attggaagac agctgtacac    900
gtcatagtgg gcccgcccgg ttgtgggaag agccagtggg cccgtaattt tgctgagcct    960
agggacacct actggaagcc tagtagaaat aagtggtggg atggatatca tggagaagaa   1020
gttgttgttt tggatgattt ttatggctgg ttaccttggg atgatctact gagactgtgt   1080
gaccggtatc cattgactgt agagactaaa gggggtactg ttccttttt ggcccgcagt   1140 attttgatta ccagcaatca ggcccccag gaatggtact cctcaactgc tgtcccagct   1200
gtagaagctc tctatcggag gattactact ttgcaatttt ggaagactgc tggagaacaa   1260
tccacggagg tacccgaagg ccgatttgaa gcagtggacc caccctgtgc ccttttccca   1320
tataaaataa attactgagt ctttttgtt atcacatcgt aatggtttt atttttattt   1380 atttagaggg tcttttagga taaattctct gaattgtaca taaatagtca gccttaccac   1440
ataattttgg gctgtggctg cattttggag cgcatagccg aggcctgtgt gctcgacatt   1500
ggtgtgggta tttaaatgga gccacagctg gtttcttta tatttgggt ggaaccaatc   1560 aattgtttgg tccagctcag gtttgggggt gaagtacctg gagtggtagg taaagggctg   1620
ccttatggtg tggcgggagg agtagttaat ataggggtca taggccaagt tggtggaggg   1680
ggttacaaag ttggcatcca agataacaac agtggaccca cacctctttt gattagaggt   1740
gatggggtct ctggggtaa                                                1759
```

<210> SEQ ID NO 6
<211> LENGTH: 1768
<212> TYPE: DNA
<213> ORGANISM: Porcine circovirus
<220> FEATURE:
<221> NAME/KEY: misc_feature
<222> LOCATION: (1)..(1768)
<223> OTHER INFORMATION: nucleotide "n" can be either of the nucleotides
      'a", "c", "g' or "t"

<400> SEQUENCE: 6

```
gaattcaacc ttaaccttt ttattctgta gtattcaaag ggtataaaga ttttgttggt     60 ccccctccc ggggaacaa agtcgtcaat attaaatctc atcatgtcca ccgcccagga    120 ggcgttctg actgtggtag ccttgacagt atatccgaag gtgcgggaga rgcgggtgtt    180
gaaaatgcca ttttccttc tccaacggta gcggtggcgg gggtggacma nccacgggcg    240
gcggcggawg atctggccaa gatggctgcg ggggcggtgt cttcttctgc ggtaacgcct    300
ccttggatac gtcatagctg aaaacgaaag aagtgcgctg taagtattac cagcgcactt    360
cggcagcggc agcacctcgg cagcacctca gcagcaacat gcccagcaag aagaatggaa    420
gaagcggacc ccaaccacat aaaaggtggg tgttcacgct gaataatcct tccgaagacg    480
agcgcaagaa aatacgggag ctcccaatct ccctatttga ttattttatt gttggcgagg    540
```

-continued

```
agggtwwtga ggaangacga acacctcacc tccagggggtt cgctaatttt gtgaagaagc      600
aaactttta  taaagtgaag tggtatttgg gtgcccgctg ccacatcgag aaagccaaag      660
gaactgatca gcagaataaa gaatattgca gtaaagaagg caacttactt attgaatgtg      720
gagctcctcg atctcaagga caacggagtg acctgtctac tgctgtgagt accttgttgg      780
agagcgggag tctggtgacc gttgcagagc agcaccctgt aacgtttgtc agaaatttcc      840
gcgggctggc tgaactttg  aaagtgagcg ggaaaatgca gaagcgtgat tggaagacca      900
atgtacacgt cattgtgggg ccacctgggg tgtaaaag   caaatgggct gctaattttg      960
cagacccgga aaccacatac tggaaaccac ctagaaacaa gtggtgggat ggttaccatg     1020
gtgaagaagt ggttgttatt gatgactttt atggctggct gccgtgggat gatctactga     1080
gactgtgtga tcgatatcca ttgactgtag agactaaagg tggaactgta cnnnnnnngg     1140
cccgcagtat tctgattacc agcaatcaga ccccgttgga atggtactcc tcaactgctg     1200
tcccagctgt agaagctctc tatcggagga ttacttcctt ggtattttgg aagaatgcta     1260
cagaacaatc cacggaggaa gggggccagt tngtcaccct ttccccccca tgccctgaat     1320
ttccatatga aataaattac tgagtctttt ttatcacttc gtaatggttt ttattattca     1380
tttagggttt aagtgggggg tctttaagat taaattctct gaattgtaca tacatggtta     1440
cacggatatt gtagtcctgg tcgtatatac tgttttcgaa cgcagtgccg aggcctacgt     1500
ggtccacatt tctagaggtt tgtagcctca gccaaagctg attccttttg ttatttggtt     1560
ggaagtaatc aatagtggag tcaagaacag gtttgggtgt gaagtaacgg gagtggtagg     1620
agaagggttg ggggattgta tggcgggagg agtagtttac atatgggtca taggttaggg     1680
ctgtggcctt tgttacaaag ttatcatcta gaataacagc agtggagccc actcccctat     1740
caccctgggt gatgggggag cagggcca                                        1768
```

<210> SEQ ID NO 7
<211> LENGTH: 1768
<212> TYPE: DNA
<213> ORGANISM: Porcine circovirus
<220> FEATURE:
<221> NAME/KEY: misc_feature
<222> LOCATION: (1)..(1768)
<223> OTHER INFORMATION: nucleotide "k" can be either "g" or "t" and
      nucleotide "y" can be either "c" or "t"

<400> SEQUENCE: 7

```
accagcgcac ttcggcagcg gcagcacctc ggcagcacct cagcagcaac atgcccagca      60
agaagaatgg aagaagcgga ccccaaccac ataaaaggtg ggtgttcacg ctgaataatc     120
cttccgaaga cgagcgcaag aaaatacggg agctcccaat ctccctattt gattatttta     180
ttgttggcga ggagggtaat gaggaaggac gaacacctca cctccagggg ttcgctaatt     240
ttgtgaagaa kcaaactttt aataaagtga agtggtattt gggtgcccgc tgccacatcg     300
agaaagccaa aggaactgat cagcagaata agaatattg  cagtaaagaa ggcaacttac     360
ttattgaatg tggagctcct cgatctcaag gacaacggag tgacctgtct actgctgtga     420
gtaccttgtt ggagagcggg agtctggtga ccgttgcaga gcagcaccct gtaacgtttg     480
tcagaaattt ccgcgggctg gctgaacttt tgaaagtgag cgggaaaatg cagaagcgtg     540
attggaagac caatgtacac gtcattgtgg ggccacctgg tgtggtaaa  agcaaatggg     600
ctgctaattt tgcagacccg gaaaccacat actggaaacc acctagaaac aagtggtggg     660
atggttacca tggtgaagaa gtggttgtta ttgatgactt ttatggctgg ctgccgtggg     720
```

```
atgatctact gagactgtgt gatcgatatc cattgactgt agagactaaa ggtggaactg      780 taccttttt  ggcccgcagt attctgatta ccagcaatca gaccccgttg aatggtact       840 cctcaactgc tgtcccagct gtagaagctc tctatcggag gattacttcc ttggtatttt      900
ggaagaatgc tacagaacaa tccacggagg aaggggggcca gttcgtcacc ctttccccc      960 catgccctga atttccatat gaaataaatt actgagtcyt ttttatcact tcgtaatggt     1020
ttttattatt catttagggg ttaagtgggg ggtctttaag attaaattcc ctgaattgta     1080 catacaggt  tacacggata ttgtagtcct ggtcgtattt actgttttcg aacgcagtgc     1140
cgaggcctac gtggtccaca tttctagagg tttgtagcct cagccaaagc tgattccttt     1200
tgttatttgg ttggaagtaa tcaatagtgg agtcaagaac aggtttgggt gtgaagtaac     1260
gggagtggta ggagaagggt tgggggattg tatggcggga ggagtagttt acatatgggt     1320
catatgtttg ggctgtggcc tttggtacaa agttatcatc tagaataaca gcagtggagc     1380
ccactcccct atcaccctgg gtgatggggg agcaggccca gaattcaacc ttaacctttc     1440
ttattctgta gtattcaaag ggtatagaga ttttgttggt cccccctccc ggggaacaa      1500 agtcgtcaat tttaaatctc atcatgtcca ccgcccagga gggcgttgtg actgtggtac     1560
gcttgacagt atatccgaag gtgcgggaga ggcgggtgtt gaagatgcca ttttccttc      1620 tccaacggta gcgtggcgg  gggtggacga gccaggggcg gcggcggagg atctggccaa     1680
gatggctgcg ggggcggtgt cttcttctgc ggtaacgcct ccttggatat gtcatagctg     1740
aaaacgaaag aagtgcgctg taagtatt                                        1768
```

<210> SEQ ID NO 8
<211> LENGTH: 1768
<212> TYPE: DNA
<213> ORGANISM: Porcine circovirus

<400> SEQUENCE: 8

```
accagcgcac ttcggcagcg gcagcacctc ggcagcacct cagcagcaac atgcccagca       60
agaagaatgg aagaagcgga cccccaaccac ataaaaggtg ggtgttcacg ctgaataatc     120
cttccgaaga cgagcgcaag aaaatacggg agctcccaat ctccctattt gattatttta     180
ttgttggcga ggagggtaat gaggaaggac gaacacctca cctccagggg ttcgctaatt     240
ttgtgaagaa gcaaactttt aataaagtga agtggtattt gggtgcccgc tgccacatcg     300
agaaagccaa aggaactgat cagcagaata agaatattg  cagtaaagaa ggcaacttac     360
ttattgaatg tggagctcct cgatctcaag gacaacggag tgacctgtct actgctgtga     420
gtaccttgtt ggagagcggg agtctggtga ccgttgcaga gcagcaccct gtaacgtttg     480
tcagaaattt ccgcgggctg gctgaacttt tgaaagtgag cgggaaaatg cagaagcgtg     540
attggaagac caatgtacac gtcattgtgg ggccacctgg gtgtggtaaa agcaaatggg     600
ctgctaattt tgcagacccg aaaccacat  actggaaacc acctagaaac aagtggtggg     660
atggttacca tggtgaagaa gtggttgtta ttgatgactt ttatggctgg ctgccgtggg     720
atgatctact gagactgtgt gatcgatatc cattgactgt agagactaaa ggtggaactg     780 taccttttt  ggcccgcagt attctgatta ccagcaatca gaccccgttg aatggtact      840 cctcaactgc tgtcccagct gtagaagctc tctatcggag gattacttcc ttggtatttt     900
ggaagaatgc tacagaacaa tccacggagg aaggggggcca gttcgtcacc ctttccccc     960 catgccctga atttccatat gaaataaatt actgagtctt ttttatcact tcgtaatggt    1020
ttttattatt catttagggg ttaagtgggg ggtctttaag attaaattct ctgaattgta    1080
```

```
catacatggt tacacggata ttgtagtcct ggtcgtattt actgttttcg aacgcagtgc    1140
cgaggcctac gtggtccaca tttctagagg tttgtagcct cagccaaagc tgattccttt    1200
tgttatttgg ttggaagtaa tcaatagtgg agtcaagaac aggtttgggt gtgaagtaac    1260
gggagtggta ggagaagggt tgggggattg tatggcggga ggagtagttt acatatgggt    1320
cataggttag ggctgtggcc tttggtacaa agttatcatc tagaataaca gcagtggagc    1380
ccactcccct atcaccctgg gtgatggggg agcagggcca gaattcaacc ttaacctttt    1440
ttattctgta gtattcaaag ggtatagaga ttttgttggt ccccctccc gggggaacaa     1500 agtcgtcaat tttaaatctc atcatgtcca ccgcccagga gggcgttgtg actgtagtac    1560
gcttgacagt atatccgaag gtgcgggaga ggcgggtgtt gaagatgcca tttttccttc    1620
tccaacggta gcggtggcgg gggtggacga gccaggggcg gcggcggagg atctggccaa    1680
gatggctgcg ggggcggtgt cttcttctgc ggtaacgcct ccttggatac gtcatagctg    1740
aaaacgaaag aagtgcgctg taagtatt                                       1768
```